(12) United States Patent
Davies

(10) Patent No.: US 11,278,214 B2
(45) Date of Patent: Mar. 22, 2022

(54) SYSTEMS AND METHODS TO DETECT AND IDENTIFY MEDICAL DEVICES WITHIN A BIOLOGICAL SUBJECT

(71) Applicant: CEREBRIA LIMITED, Herts (GB)

(72) Inventor: Helen Davies, London (GB)

(73) Assignee: CEREBRIA LIMITED, Herts (GB)

( * ) Notice: Subject to any disclaimer, the term of this patent is extended or adjusted under 35 U.S.C. 154(b) by 993 days.

(21) Appl. No.: 15/753,395

(22) PCT Filed: May 13, 2016

(86) PCT No.: PCT/GB2016/051382
§ 371 (c)(1),
(2) Date: Feb. 19, 2018

(87) PCT Pub. No.: WO2016/185180
PCT Pub. Date: Nov. 24, 2016

(65) Prior Publication Data
US 2019/0008412 A1 Jan. 10, 2019

(30) Foreign Application Priority Data
May 15, 2015 (GB) .................................. 1508400
Sep. 25, 2015 (GB) .................................. 1516990

(51) Int. Cl.
*A61B 90/96* (2016.01)
*A61B 5/06* (2006.01)
(Continued)

(52) U.S. Cl.
CPC ............ *A61B 5/06* (2013.01); *A61B 5/0059* (2013.01); *A61B 6/12* (2013.01); *A61B 6/504* (2013.01);
(Continued)

(58) Field of Classification Search
CPC .................................................. G06K 7/1426
See application file for complete search history.

(56) References Cited

U.S. PATENT DOCUMENTS

2006/0212096 A1 9/2006 Stevenson
2007/0016244 A1* 1/2007 Behl ..................... A61M 25/04
606/200
(Continued)

FOREIGN PATENT DOCUMENTS

KR 101 065 299 B1 9/2011
WO WO-2006/101993 A2 9/2006
WO WO-2012/090148 A1 7/2012

OTHER PUBLICATIONS

International Search Report and Written Opinion for Application No. PCT/GB2016/051382, dated Jul. 12, 2016.

*Primary Examiner* — Keith M Raymond
*Assistant Examiner* — Colin T. Sakamoto
(74) *Attorney, Agent, or Firm* — Marshall, Gerstein & Borun LLP

(57) ABSTRACT

A system to detect a medical device within a biological subject, the system comprising: an imaging system operable to generate image data derived from the biological subject and image data derived from the medical device; and a processor operable to detect the medical device and evaluate the image data derived from the medical device to identify the nature of the medical device. Further, a system to match a signature from a detected medical device within a biological subject with signature information held in a databank for a plurality of medical devices, the databank also holding specification information corresponding to the plurality of medical devices, the system being operable to match a signature relating to a detected medical device with signature information held in the databank and to provide some or
(Continued)

all of the specification information for the matched signature to identify the nature of the medical device.

20 Claims, 23 Drawing Sheets

(51) Int. Cl.
    *A61B 90/00*      (2016.01)
    *A61B 6/12*      (2006.01)
    *A61B 5/00*      (2006.01)
    *A61B 90/90*      (2016.01)
    *A61B 6/00*      (2006.01)
    *A61B 8/08*      (2006.01)
    *A61B 6/03*      (2006.01)
    *G06T 7/00*      (2017.01)

(52) U.S. Cl.
    CPC ............ *A61B 8/5207* (2013.01); *A61B 90/39* (2016.02); *A61B 90/90* (2016.02); *A61B 90/96* (2016.02); *A61B 6/032* (2013.01); *A61B 6/487* (2013.01); *A61B 2090/3925* (2016.02); *A61B 2090/3937* (2016.02); *A61B 2090/3966* (2016.02); *G06T 7/0012* (2013.01); *G06T 2207/10081* (2013.01); *G06T 2207/10088* (2013.01); *G06T 2207/10121* (2013.01); *G06T 2207/10132* (2013.01)

(56) References Cited

U.S. PATENT DOCUMENTS

| | | | |
|---|---|---|---|
| 2009/0171196 A1* | 7/2009 | Olson | A61B 90/96 600/426 |
| 2010/0131023 A1 | 5/2010 | Costello et al. | |
| 2013/0184571 A1 | 7/2013 | Wilkening et al. | |
| 2014/0135619 A1* | 5/2014 | Casanova | A61F 2/06 600/424 |
| 2014/0263674 A1* | 9/2014 | Cerveny | G06K 19/06037 235/494 |
| 2015/0088091 A1* | 3/2015 | Beasley | A61M 25/00 604/506 |
| 2015/0254542 A1* | 9/2015 | Deffeyes | G06K 19/0614 235/462.04 |
| 2016/0042261 A1* | 2/2016 | Kieser | G06K 19/06121 235/489 |

* cited by examiner 4 greyscales :  0 : 100% opacity
              1 : 66% opacity
              2 : 33% opacity
              3 : 0% opacity 3 greyscales :  0 : 100% opacity
              1 : 50% opacity
              2 : 0% opacity

SYSTEMS AND METHODS TO DETECT AND IDENTIFY MEDICAL DEVICES WITHIN A BIOLOGICAL SUBJECT

BACKGROUND TO THE INVENTION

The present invention relates to systems and methods to detect and identify medical devices within a biological subject.

Medical devices such as catheters and balloons are inserted into patients and guided around the body along major blood vessels to a destination location where treatment or investigation is to take place. Various imaging techniques can be used to guide and verify the location of the medical device (or part of the medical device). For example, x-ray guidance is commonly used. The treatment of the patient may involve a medical device being left behind at the treatment site, for example, a stent.

Frequently, it is difficult to know what equipment has been used in each case, especially if the patient was treated somewhere else previously or their medical notes are out of date or incorrect. Manual documentation is used to track what medical devices have previously been used. That documentation is not always available and may not necessarily be correct.

In other scenarios, devices are implanted such as pacemakers or hip replacements and it is difficult to know what device, model or size is used afterwards if the manual documentation is not available or correct.

Product recalls on medical devices such as artificial hip joints or silicone breast implants can occur. The medical device needs to be identified to determine whether it is in the class of products being recalled. Having to undertake an invasive procedure to identify the medical device and thus determine whether it needs to be replaced or not, presents a significant risk to the patient. Any invasive procedure, merely to reliably identify a medical device within a patient, is difficult to justify.

Software solutions are available in combination with ultrasound techniques to distinguish and recognize specific arteries, for example, the common carotid artery, and then determine physical properties of the artery such as lumen diameter and wall thickness. Software solutions are also available to help recognize medical devices such as hip replacements from their geometric shapes and dimensions.

SOME ASPECTS OF THE INVENTION

One aspect of the invention provides a system to detect a medical device within a biological subject and identify the medical device, the system comprising:
  an imaging system operable to generate image data derived from the biological subject and image data derived from the medical device within the biological subject; and
  a processor operable to evaluate the image data derived from the medical device to detect and identify the medical device, wherein:
  the medical device has a marker and the image data derived from the medical device is image data of the marker, and
  the opacity of the marker to the imaging system is modulated to encode information in the marker.

Another aspect of the invention provides a system to detect a medical device within a biological subject, the system comprising:
  a processor operable to:
    receive image data derived from the biological subject and image data derived from the medical device;
    detect the medical device and
    evaluate the image data derived from the medical device to identify the nature of the medical device.

Another aspect of the invention provides a system to match a signature from a detected medical device within a biological subject with signature information held in a databank for a plurality of medical devices, the databank also holding specification information corresponding to the plurality of medical devices, the system being operable to match a signature relating to a detected medical device with signature information held in the databank and to provide some or all of the specification information for the matched signature to identify the nature of the medical device.

Another aspect of the invention provides a marker for attachment to, embedding in or comprising a medical device to identify the medical device from imaging data of the marker, the marker having information encoded in the opacity of the marker to an imaging system.

Another aspect of the invention provides a method of detecting a medical device in a biological subject, the method comprising:
  imaging the biological subject;
  generating image data derived from the biological subject;
  generating image data derived from the medical device;
  processing the image data to detect the medical device; and
  determining the nature of the medical device.

Another aspect of the invention provides a method of matching a signature from a detected medical device within a biological subject with signature information held in a databank for a plurality of medical devices, the databank also holding specification information corresponding to the plurality of medical devices, the method comprising:
  matching a signature relating to a detected medical device with signature information held in the databank;
  providing some or all of the specification information for the matched signature to identify the nature of the medical device.

Another aspect of the invention provides a method of augmenting image data of a biological subject and a medical device within the biological subject comprising:
  deriving a signature from the medical device;
  interrogating a databank holding specification information corresponding to a plurality of medical devices;
  matching the signature from the medical device with signature information held in the databank;
  providing some or all of the specification information for the matched signature to augment the image data.

One aspect of the present invention provides a system to detect a medical device within a biological subject, the system comprising: an imaging system operable to generate image data derived from the biological subject and image data derived from the medical device; and a processor operable to detect the medical device and evaluate the image data derived from the medical device to identify the nature of the medical device.

Another aspect of the present invention provides a marker and the image data derived from the medical device is image data of the marker, the system being operable to generate a signature from the marker image data, the signature being related to the detected medical device.

A further aspect of the present invention provides the material of the marker, the marker surface texture, marker surface contour or other property of the marker is modulated to encode information in the marker and the modulation is apparent to an imaging system operable to generate the image data derived from the biological subject and/or the modulation is apparent to an imaging system operable to generate the image data derived from the medical device.

In another aspect of the present invention, the medical device has characteristics and the image data derived from the medical device is image data of the medical device characteristics, the system being operable to generate a signature from the characteristics, the signature being related to the detected medical device.

Another aspect of the present invention provides a databank holding signature information for a plurality of medical devices and corresponding specification information and/or characteristics for the plurality of medical devices, the system being operable to match a signature relating to a detected medical device with signature information held in the databank and to provide some or all of the specification information for the matched signature.

A further aspect of the present invention augments the image data with some or all of the specification information for the matched signature, the augmenting information being in respect of and/or associated with the detected medical device.

A further aspect of the present invention provides a module operable to recognise a site in the subject or a body part of the subject.

In another aspect of the present invention, the module is further operable to determine the location of the detected medical device with respect to the recognised site in the subject or body part of the subject.

In a further aspect of the present invention, the system is operable to further augment the augmented image data with: the site in the subject or a body part of the subject; and/or the location of the detected medical device with respect to the recognised site in the subject or body part of the subject.

Another aspect of the present invention provides a system to detect a medical device within a biological subject, the system comprising: a processor operable to: receive image data derived from the biological subject and image data derived from the medical device; detect the medical device and evaluate the image data derived from the medical device to identify the nature of the medical device.

A further aspect of the present invention provides a system to match a signature from a detected medical device within a biological subject with signature information held in a databank for a plurality of medical devices, the databank also holding specification information corresponding to the plurality of medical devices, the system being operable to match a signature relating to a detected medical device with signature information held in the databank and to provide some or all of the specification information for the matched signature to identify the nature of the medical device.

Another aspect of the present invention provides a method of detecting a medical device in a biological subject, the method comprising: imaging the biological subject; generating image data derived from the biological subject, generating image data derived from the medical device; processing the image data to detect the medical device; and determining the nature of the medical device.

A further aspect of the present invention provides a method of matching a signature from a detected medical device within a biological subject with signature information held in a databank for a plurality of medical devices, the databank also holding specification information corresponding to the plurality of medical devices, the method comprising: matching a signature relating to a detected medical device with signature information held in the databank; providing some or all of the specification information for the matched signature to identify the nature of the medical device.

Another aspect of the present invention provides a system to match a method of augmenting image data of a biological subject and a medical device within the biological subject comprising: deriving a signature from the medical device; interrogating a databank holding specification information corresponding to a plurality of medical devices; matching the signature from the medical device with signature information held in the databank; and providing some or all of the specification information for the matched signature to augment the image data.

BRIEF DESCRIPTION OF EMBODIMENTS OF THE INVENTION

So that the present invention may be more readily understood, embodiments of the present invention will now be described, by way of example, with reference to the accompanying drawings, in which.

DETAILED DESCRIPTION OF EMBODIMENTS OF THE INVENTION

A medical practitioner reviewing a patient or performing a procedure on a patient needs to have accurate and up to the minute information about the patient's status and this includes the medical devices present already in the patient and those being introduced to the patient in an ongoing procedure. More than one medical device may be in the field of view of the image of the procedure or review. It is also useful for the practitioner to be aware of the proximity of other medical devices in case there is any possibility of migration, collision or interference between devices. It is also useful for a practitioner to be able to evaluate whether other medical devices shown in image data of a procedure are relevant or not to an ongoing procedure. For example, if an image showed a stent present in one artery and the practitioner is introducing a stent in a distinct artery, then even though the two stents may be shown in the image as in proximity to one another their proximity can be disregarded since the arteries are at different levels or layers in the image. Embodiments of the invention allow such disambiguity considerations to be evaluated by the practitioner in real time.

When retrieving or replacing a medical device implanted in a patient, for example because of a product recall or routine replacement, it is good practice to retrieve and replace the correct medical device. Embodiments of the invention allow the correct device to be identified, recognised and importantly, verified by virtue of the practitioner being provided with real time augmenting information, for example, overlaying and pointing to and labelling up the medical devices being imaged.

Figure 1:
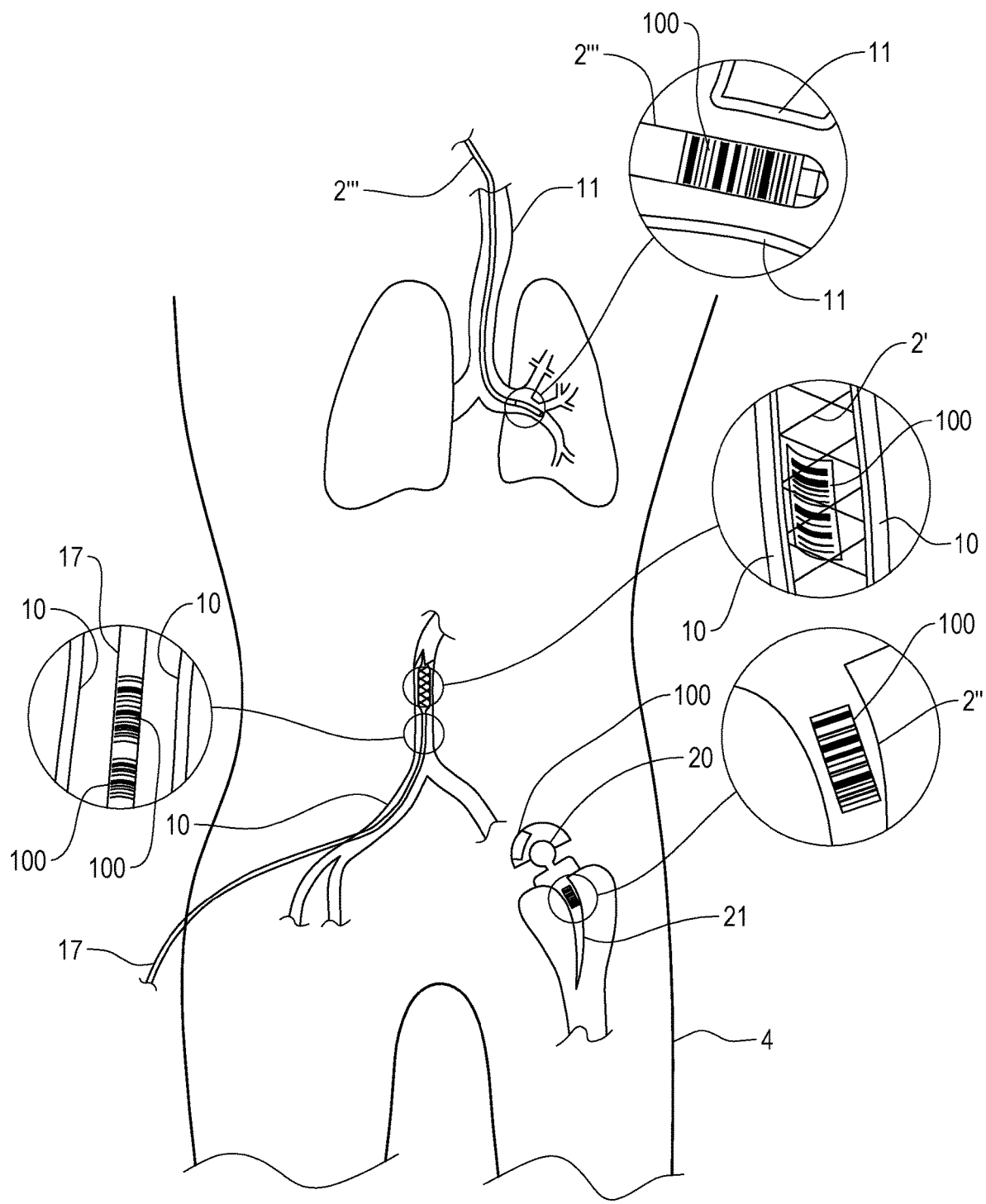
FIG. 1 is a schematic representation of a patient with a stent, a bronchoscope inserted in the trachea and a replacement hip joint prosthesis.
Figure 2:
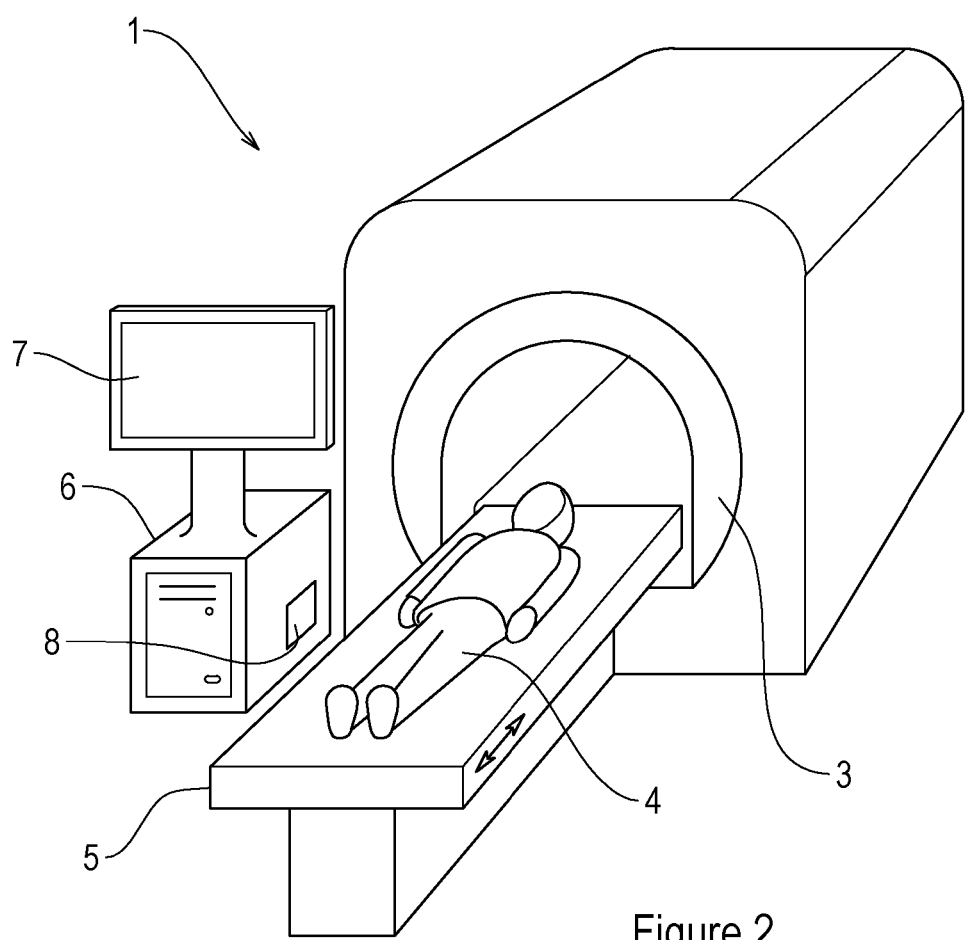
FIG. 2 is a schematic representation of a system embodying the present invention.

System: Referring to FIGS. 1 and 2, a system 1 embodying the present invention to detect medical devices 2 within a biological subject like the human or an animal body 4 comprises one or more imaging systems 3 containing the mechanics to image within a human body 4, a movable platform 5 on which the patient is placed in a prone position to be imaged and a processor 6 which provides image processor functionality to analyse the images and/or image data provided by the imaging systems 3 and which detects and preferably identifies medical devices 2 located within the body 4 of a patient. In these examples, a human body is illustrated but the invention is applicable to other biological subjects. An augmented image or image data is produced by the system and the augmented image can be rendered on a display 7.

Figure 3:
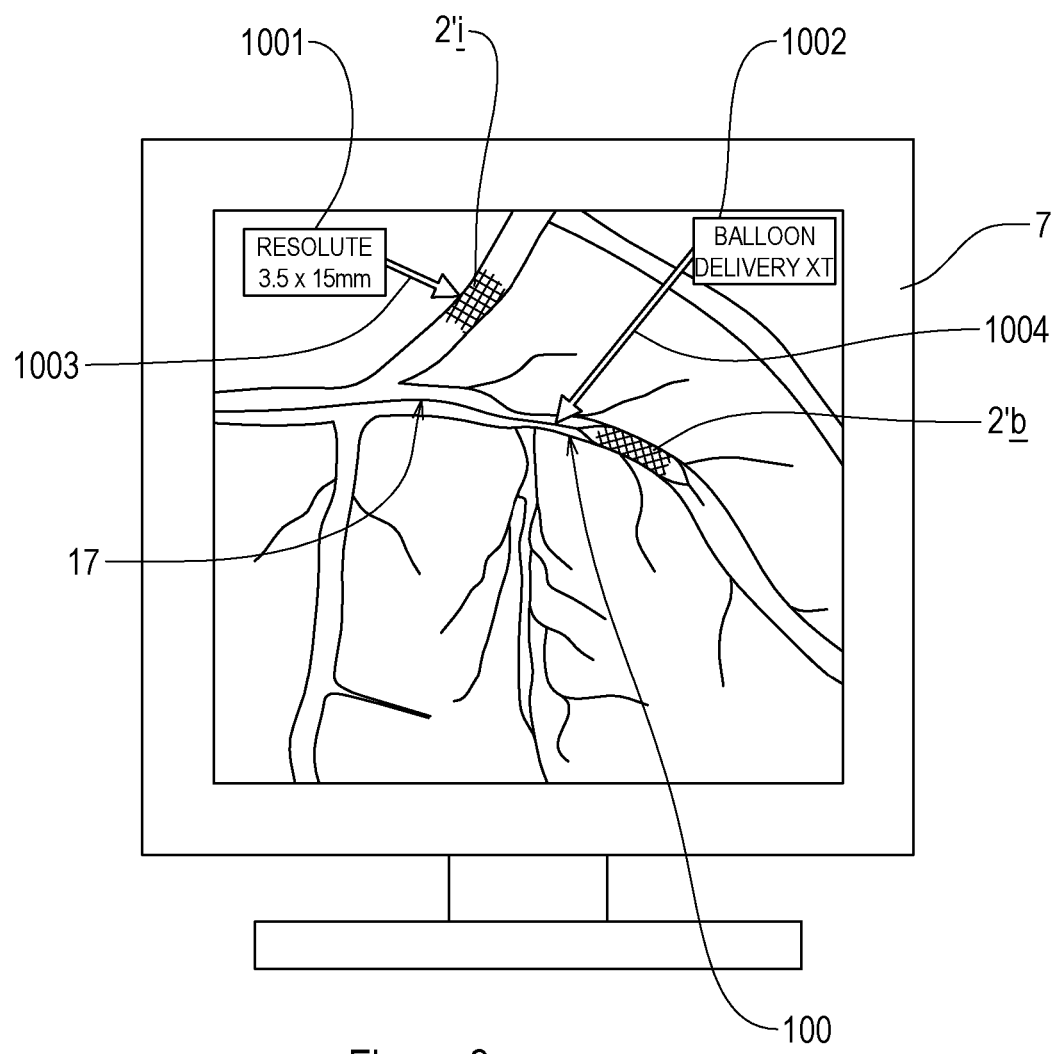
FIG. 3 is a schematic example of an augmented image produced by embodiments of the invention.

Augmenting information: FIG. 3 shows an augmented image produced in accordance with one embodiment of the present invention. The image schematically shows the original image data of blood vessels and medical devices implanted in those blood vessels. The medical devices are two stents 2'. One stent 2'i has been implanted in a blood vessel and the other stent 2'b is carried on a balloon delivery device 17 and is being deployed at a body site in another blood vessel. The implanted stent 2'i is recognised by the system embodying the present invention by pattern recognition techniques (discussed later) based on characteristics derived from the image data of the medical device. The stent 2'b being deployed by a balloon is recognised by a different mechanism. The balloon delivery shaft has a marker 100 which helps to identify the balloon and the associated stent 2'b. Recognising the balloon by the marker it carries is a recognition technique which is discussed later.

The image in FIG. 3 is augmented by data linked to the particular medical devices 2 identified in the image. The implanted stent 2'i is determined by the system embodying the present invention to be, for example, 23232321DDX SDS223 CORONARY RESOLUTE Medtronic™ (3.5×15 mm) stent. This augmenting information (or part of this information) 1001 is displayed by the system and, in this example, overlays the original image. The balloon delivery system is similarly labelled up by the system embodying the present invention as a "Balloon Delivery XT" device and this information (or part of this information) 1002 is also displayed by the system. Other mechanisms for providing augmented information (and delivering it to displays, third parties, reports) are discussed later in the specification.

Preferably the augmenting information 1001,1002 or the "label" providing the augmenting information provides a pointer 1003, 1004 to the respective medical device which the system has recognised.

Overlaying the augmenting information on the original image as in FIG. 3 is a preferred embodiment of the present invention. An augmented image or image data is produced by the system and the augmented image can be rendered on a display 7. Alternatively, or in addition, the augmenting information can be provided by the system to be recorded or logged in a data storage medium and may itself be used to further populate a record associated with a patient or a record associated with a medical device. The record may also be populated with the image data, augmented or original. This provides a linked intelligent data gathering system.

Medical devices: Medical devices 2 can be implanted in the biological subject or be present temporarily as, for example, part of a delivery mechanism. The medical devices may not have a medical function but are termed medical devices for the purpose of this discussion since they are implanted within the human body. An example of a medical device without a medical function is a surgically implanted RFID tag serving to identify the subject, for example a canine RFID chip.

FIG. 1 shows a hypothetical patient having, within their body 4: a balloon deployment guided lead 17 carrying an inflatable balloon 18 with an implantable stent 2' to be permanently deployed in the aorta 10 (a blood vessel); a replacement hip joint prosthesis 2" having a femoral head part 20 and a femoral stem 21; and a bronchoscope 2'" inserted in their trachea 11. The bronchoscope 2'", the lead 17 and the balloon 18 are not permanently implanted but are present during the active procedure.

Imaging systems: Imaging of the human body and medical devices within the body is accomplished by a number of different imaging system 3 mechanisms such as x-ray imaging, CT scans, magnetic resonance imaging (MRI), ultrasound techniques, functional medical imaging, fluoroscopy techniques, IVUS (intravascular ultrasound), OCT (optical coherence tomography) and various other tomography techniques. Some imaging techniques are more suited than others for imaging particular targets. The available imaging techniques can be combined with one another to provide composite images and/or data from one imaging technique is used to inform the data from another imaging technique. These techniques can be used to provide image data and/or images to image processing systems. The imaging system may comprise multiple different forms of imaging. Preferably, if there are multiple imaging systems 3 employed in the system 1, then the areas which they image coincide or overlap so that an overlapping portion provides a composite image in which the two or more images are aligned. Some imaging systems 3 image in a plane 20. The imaging systems generate image data generate image data derived from the biological subject and image data derived from the medical device located within the subject—the so-called original image data.

Recognition and identification (non-marker imaging recognition—pattern recognition techniques): Medical devices are not usually fabricated from human tissue and therefore they present themselves, when imaged, as being distinct from human tissue. Medical devices located within the human body have characteristics that are distinct from the human tissue surrounding them. For example, medical devices like replacement hip joints are manufactured from material which is more dense and more homogenous than human tissue and are therefore readily visible when imaged.

Imaging of the characteristics of a medical device enable an imaged device to be recognized by the system embodying the present invention. The image recognition functionality is provided by the processor 6. For example, characteristic features like the density or shape of an object can be used to recognize the device as a catheter 17, a bronchoscope 2''', a balloon 18, a stent 2', a replacement joint 2" or other device. The device 2 can be permanently implanted in an invasive procedure or can be present temporarily in the course of a procedure. Recognition techniques can use machine learning techniques such as pattern recognition, pattern matching, shape matching which may use fuzzy logic, neural networks and heuristics. These characteristics of medical devices 2 are used to generate signatures of respective medical devices so that medical devices having matching signatures can be detected and also possibly identified.

FIGS. 5 to 8 show various medical devices and their characteristics to aid/infer recognition by shape, strut number, form, size, configuration, relative dimensions and/or with marker according to examples of the present invention. These different characteristics of the medical devices each generate distinct signatures. In some embodiments, detection comprises the successful reading of characteristics from the medical device, which characteristics can be used to generate a signature corresponding to that medical device (or class of medical devices). The signature may identify the class of product of the medical device. The signature may be a unique identifier of the detected medical device.

The signature is checked against a register containing records of signatures and the register is held in a databank 8.

In the case of a stent, recognition can be achieved by analyzing the number of cells or struts or by a combination of both.

In the case of a pacemaker or replacement joint, by studying the shape and/or outline of the pacemaker or prosthetic joint replacement.

Recognition and identification (non-marker imaging recognition): Instead of (or in addition to) conducting detection of medical devices by shape recognition, as above, detection can also be achieved in embodiments of the invention using a marker 100 to aid or infer recognition. Medical devices 2 may be provided with a marker 100 to assist recognition and/or to provide an identifier. The marker 100 can be in the form of a bar code label or insert 101, or similar other identifier designed to label or encode a medical device 2 using an imaging modality such as X-Ray (fluoroscopy, computer tomography, CT scan or MRI), ultrasound or other such modality. The identifier may offer a unique identifier for each medical device 2 or may be an indicator of the class of medical device or can be both a class indicator and an individual identifier (or unique serial number). The marker 100 can be implemented as an x-ray or ultrasound-readable barcode. The marker is preferably machine readable. The marker is suitable for attachment to a medical device, for embedding in a medical device or the marker actually comprises the medical device. Imaging data from the marker identifies the medical device. The marker is preferably radiopaque or has one or more parts of respective radiopacity so that information can be encoded in the relative opacity of the marker to the imaging system.

Many coding schemes using portions of the marker material (or medical device material) which are opaque to the respective imaging system and contrasting portions which are non-opaque or partially-opaque to the respective imaging system are available to those skilled in applying codes to materials. For example, in the case of x-ray derived imaging an x-ray-readable barcode or other such marker is made up from alternating bars of varying thickness of radio-opaque and non-radio-opaque portions. In another example, the marker is a string of radio-opaque bits and non-radio-opaque bits. The radio-opaque bits are 1's or 0's and conversely non-radio-opaque bits are 0's or 1's thereby delivering binary code information. Effectively, the material of the medical device, its surface texture or some other property of the material is modulated to embody the code and that modulation is "visible" or apparent to the imaging system being used to provide the image data.

The opacity of the material of the marker, the opacity of the marker surface texture, the opacity of the marker surface contour or other property of the marker is modulated to encode information in the marker and this modulation is apparent to the imaging system being used to generate the image data derived from the biological subject and/or the modulation is apparent to the imaging system being used to generate the image data derived from the medical device—the respective imaging systems may be the same imaging system or different imaging systems.

Figure 9:
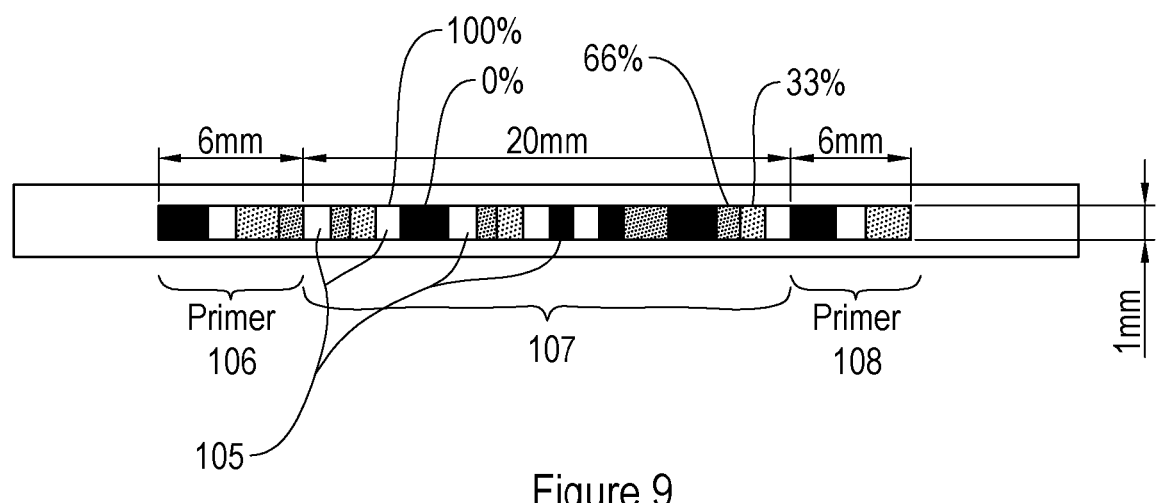
FIG. 9 is a schematic example embodying the present invention of a marker carrying a code.

In one embodiment, the marker is a barcode applied to (or part of) the shaft of the balloon delivery system or even on the balloon or stent itself. In another embodiment, information is encoded as a digital watermark image on or in the medical device—the marker is a digital watermark image. A digital watermark image is not a code per se. In one example, a digital watermark presents a known image in a slightly different manner and the information in the watermark is conveyed by deriving the difference features from the known image. The differences in radiopacity in areas of the marker may be slight, imperceptible to the naked eye, for example, but perceptible to high resolution medical imaging equipment. The marker may be a code of a series of bits—each bit in FIG. 9 is a block or strip and the code is a linear array of bits (along the x-axis, say) like a barcode. The stacked layers of radiopaque material can make bits of different value. The bits are stacked in the z-axis, say. The bits can be offset from one another. The marker can be a 2D data matrix like a QR code with multiple layers. The marker can be a 2D data matrix with only two levels of radiopacity—a binary code or data matrix.

When the marker is configured as a more complex code, the more complex codes can include orientation information which may be valuable when attempting to interrogate a code which is not being presented square on to the image capture device and/or can provide information about the orientation of the marked medical device within the body.

In the case of ultrasound, a similar barcode or other such marker composed of textured markers, or markers with different acoustic or reflective properties differentially scatters ultrasound waves. This ultrasound-readable pattern is detected and presented to a databank.

There may be more than one medical device within a patient so the system is able to process either serially or in parallel each of the medical devices. Of course, if the volume of the patient which is imaged is limited (and not a full body scan), then only those medical devices within the imaging footprint will be detected.

When a body is scanned or imaged by the system embodying the present invention, one or markers may be detected if they are present in the body. In some embodiments, detection comprises the successful reading of information from a marker 100. Preferably, the marker is machine readable. Preferably, the machine reading the marker is one of the imaging systems 3. The information conveyed by the marker 100 is, or results in the generation of, a signature comprising the whole or part of the information conveyed by the marker 100. The signature is an output of the image processor 6. The signature can be a hash of the marker identifier. The signature may identify the class of product of the medical device. The signature may be a unique identifier of the detected medical device.

The signature is checked against a register containing records of signatures and the register is held in a databank 8.

Figure 4:
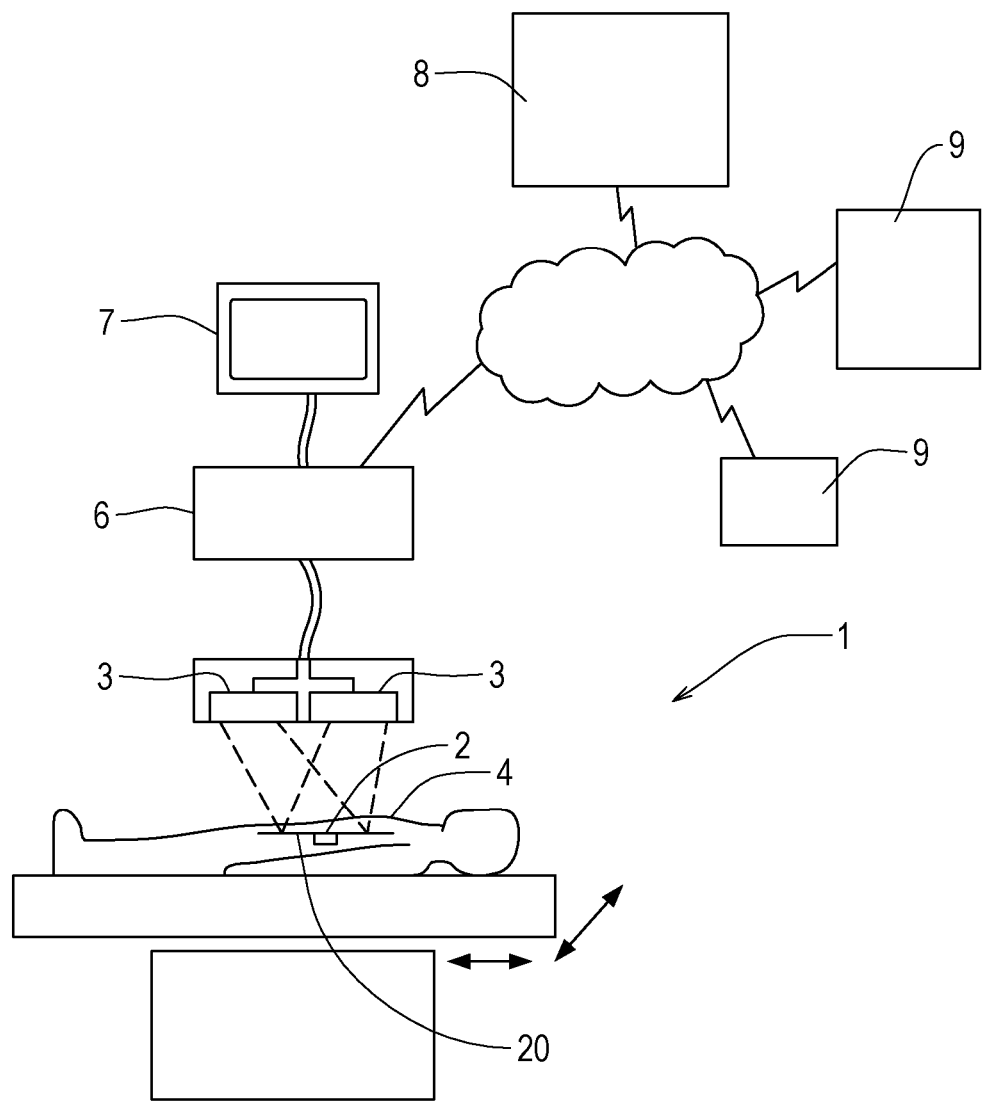
FIG. 4 is a schematic representation of a system embodying the present invention.
Figure 5:
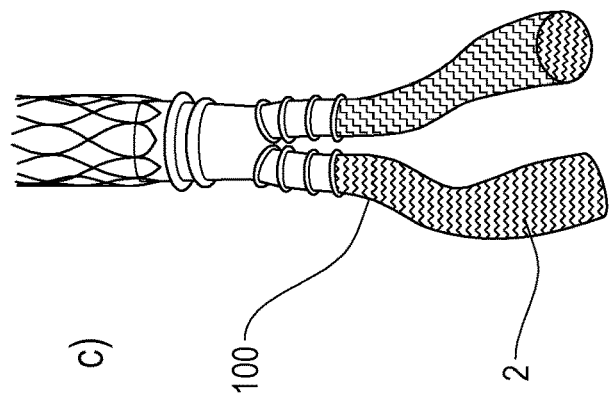
FIGS. 5 to 8 show various medical devices and their characteristics to aid/infer recognition by shape, strut number, form, size, configuration, relative dimensions and/or by marker according to examples of the present invention.
Figure 5:
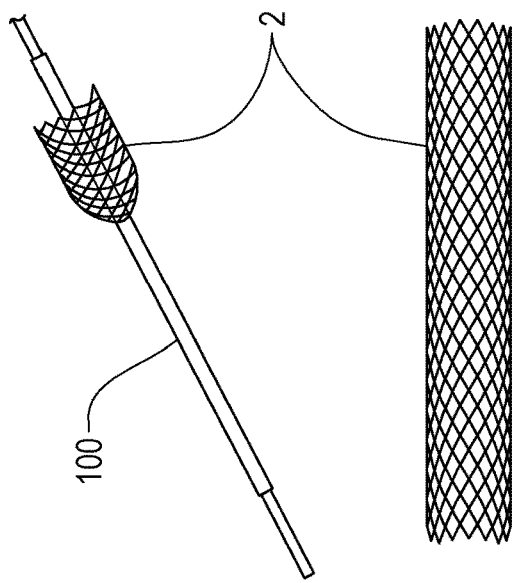
Figure 6:
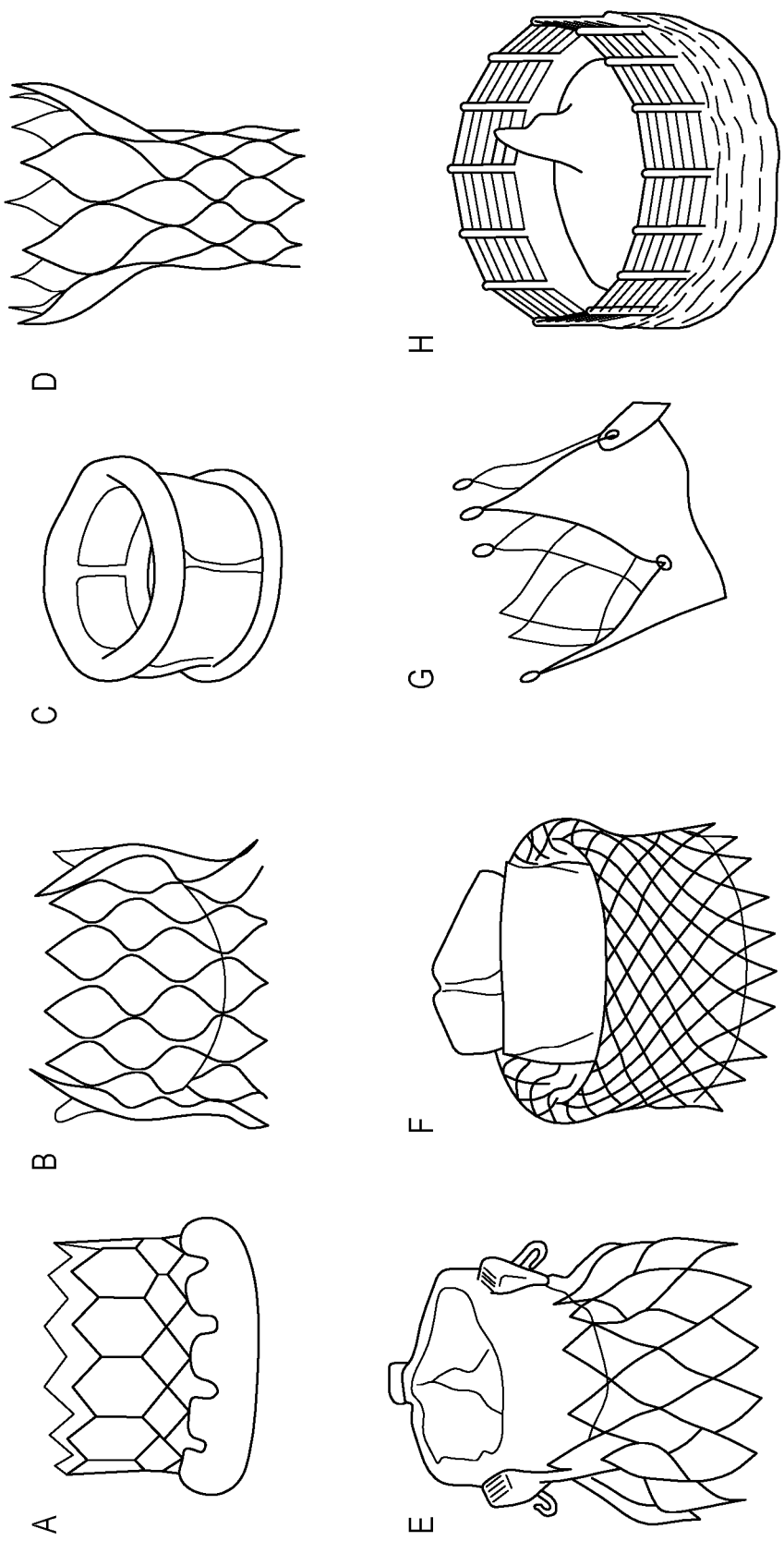
Figure 7:
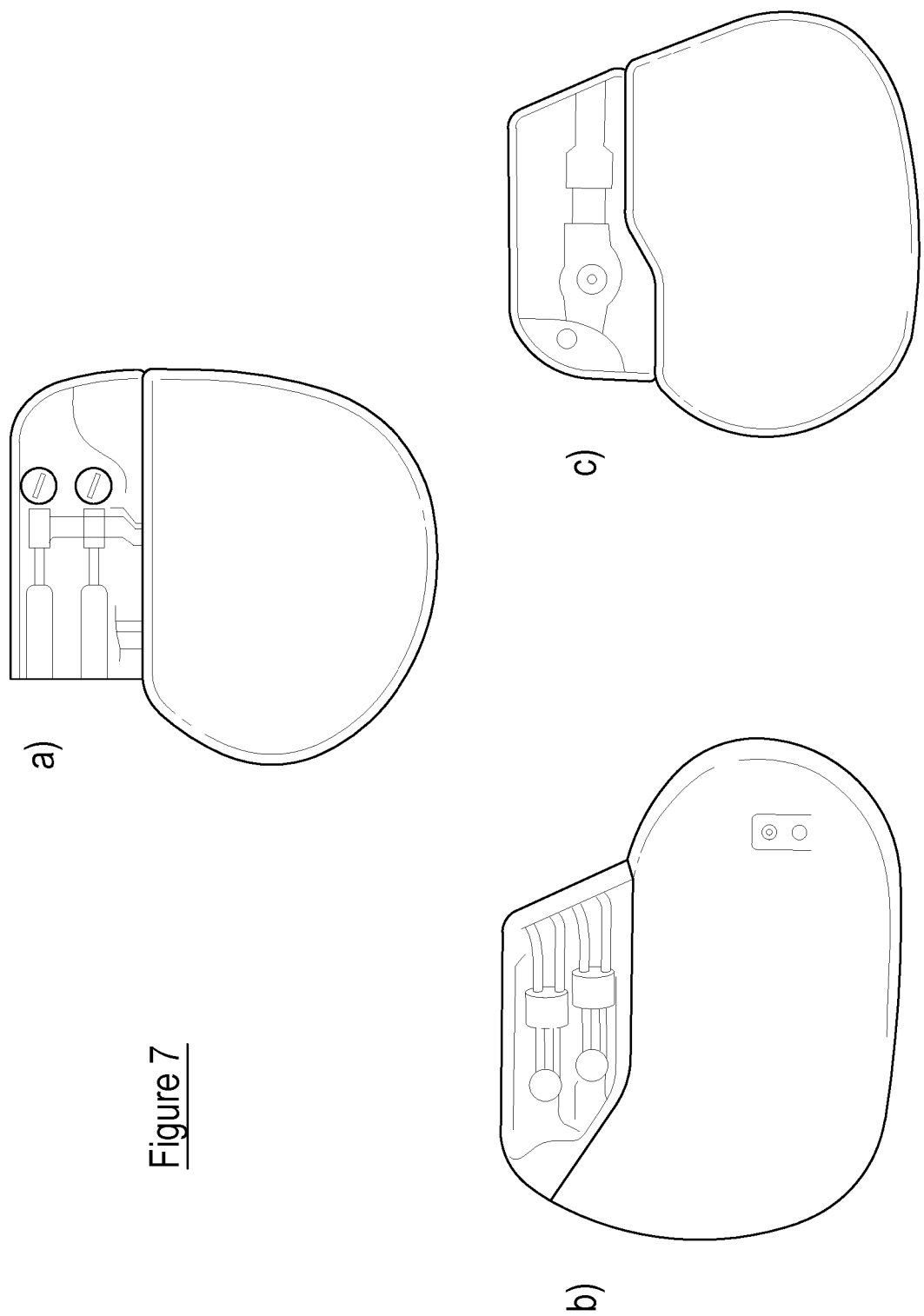
Figure 8:
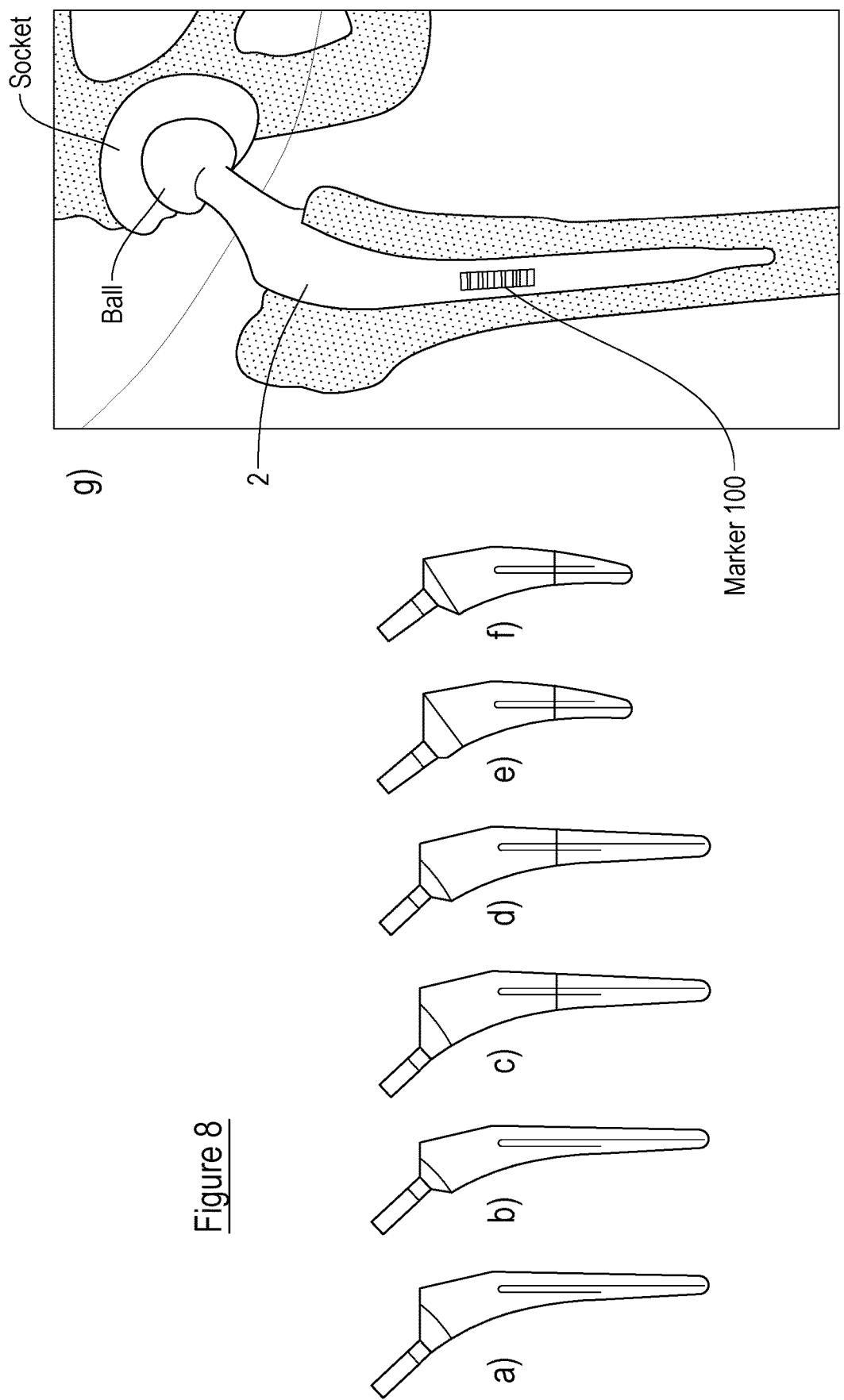

Processor: The processor 6 in the FIG. 2 embodiment of the invention is shown as local to the imaging system 3. In some embodiments of the invention, the various functions performed by the processor 6 can be distributed with some or none being local to the imaging system 3 and some or all being remote from the imaging system 3. In some examples of distributed processor function, the remote location can be one or more third party sites 9 as shown in the FIG. 4 example.

Databank: The databank 8 is held locally on the system embodying the present invention as in the FIG. 2 example, or is held remotely from the imaging system 3 but in communication with the system as shown in the FIG. 4 example. In the case of a remote databank 8, see FIG. 4 example, the system accesses the databank 8 by way of regular downloaded updates or on demand/polling.

The databank 8 contains a record of marker signatures or shape/pattern signatures that are compared to either: the images or image data derived from the imaged device; and/or the marker information derived from the medical device. The databank can operate as a lookup table so that when a match between the information derived from the medical device and the signatures in the databank is discovered, the databank 8 holds key information identifying the matched device and is operable to provide specification information for that medical device such as its manufacturer, date of manufacture, location of manufacture, batch number, size and a listing of the sub-assembly parts and the materials of manufacture. This list is not intended to be exclusive and other properties or characteristics of the medical device can be held on the databank. In some embodiments, the specification information includes a link or URL pointing the databank enquiry to a third party online resource 9, maintained, for example, by a manufacturer or health authority. An example of specification information for a number of hypothetical medical devices 2 denoted by their respective signatures is shown in Table 1:

The databank 8 returns the identity of the marker 100 and/or all or part of the specification information for that medical device 2 to the system so that the system can convey that information to the system operator or perhaps also to a third party 9 such as the manufacturer or a medical panel/watchdog/health authority.

The system embodying the present invention then has specification information about the medical device(s) detected in the patient. This specification information (or a selection of this information) can then be:

presented to the system operator by addition of the information to the imaging report;

passed onto a third party 9 software platform for incorporation of the identified medical device and/or its information into a report (such as adding the specification information to the patient's electronic medical notes); and/or displaying the medical device's specification information directly on the system screen 7—the scanned image of the device can be presented or a render of an image of the recognized medical device is presented.

Preferably, the image data is displayed and is augmented by the medical device specification information, very valuable information for the operator and/or medical practitioner. The augmentation may comprise rendering a schematic representation of the recognised medical device 2 and/or "labelling-up" the original image data with a descriptor giving some or all of the recognised medical device's specification information.

Advantageously, alternatively, or in addition, to augmenting the original image data, the augmenting information can be provided for recordal or logging in a data storage medium which may or may not be the databank 8. The augmenting information in combination with some or all of the image data from which the matched signature was derived may itself be used to further populate a record associated with a patient or a record associated with a medical device. The record may also be populated with the image data, as augmented or as the original image data. This provides a linked intelligent data gathering system.

Recognising the site in the human body of the medical device: Examples of the invention include module solutions which operate in concert with the imaging technologies used by the imaging system embodying the present invention to distinguish between and recognise body parts or sites in the body. Specific blood vessels, for example, the common

TABLE 1

| Signature | Class | Identity | Manufacturer | Size |
|---|---|---|---|---|
| 23F437D38A | Stent | 1001.00234 | Stents Inc. | n/a |
| 42F43AD27 | Balloon | 1001.00947 | Inflate Co. | n/a |
| 43F54A | Prosthesis | 2010.00032 | Regenerate Ltd. | 28 mm head |

| Signature | Date of implant | Patient identifier (anonymised) | Sub-assemblies | Batch | Date of Manufacture | Location of manufacture |
|---|---|---|---|---|---|---|
| 23F437D38A | 30/02/2018 | Joe Bloggs | 1001.01 | 324B6 | 30 Feb. 2016 | London, UK |
| 42F43AD27 | n/a | John Doe | 1001.94 | 4B567 | 30 Feb. 2016 | Penang, MY |
| 43F54A | 31/02/2018 | Ade Body | n/a | 8F432 | 30 Feb. 2016 | Untitled, US |

| Signature | FDA Approval USFDA Reg no. | CE Mark | Material information |
|---|---|---|---|
| 23F437D38A | 34212/2016 | n/a | https://linkto3rdparty1.com |
| 42F43AD27 | 53322/2016 | n/a | https://linkto3rdparty2.com |
| 43F54A | 95032/2016 | CE2016/3214 | https://linkto3rdparty3.com | carotid artery, can be distinguished from one another and recognized by existing software modules. Such modules can then determine the physical properties of the artery such as lumen diameter and wall thickness. The software solutions allow for the recognition of parts of the human body such as specific organs and, because the system embodying the present invention is also able to identify and image the detected medical devices, a useful disambiguity function is enabled Embodiments of the invention use information derived from the image processor and/or the specification information returned from the databank 8 for detected medical devices to recognise (or help recognise or infer recognition of) a part of the human body subject or a site in the body and can then also determine the location of the detected medical device with respect to the recognised part of the human body subject or the recognised site in the body.

The part of the human body or site in the human body does not need to be recognised, as such, as recognition can be inferred from the nature of the medical device, by the class of the medical device, by the identity of the medical device and by the size, shape and/or construction of the medical device either as recognised directly from the imaging system and/or from the specification information returned from the databank 8. For example, a bronchoscope is more likely to be in the trachea than a stent so if a medical device is detected in the stent class, then it can be inferred that the stent is in a blood vessel and not the trachea.

Thus, the identification of the medical device 2 by its marker 100 and/or by the returned specification information from the databank 8 aids recognition of the body part or site in the human body itself. For example, from a computational perspective, this further information would be extremely helpful in recognising a coronary artery from a carotid. Of course in many cases the device may not be left in situ, as the marker might be on the delivery balloon shaft rather than on the stent, but that data could still be captured.

For example, stents will most frequently be located in blood vessels and not, for example, in the trachea, so if the imaging system "sees" a stent, then the system therefore "knows" because it has identified the medical device as a stent that the part of the body in which the stent is located must be a blood vessel and not the trachea. Furthermore, because the system is able to distinguish between blood vessels and identify specific blood vessels, a rendering (possibly "labelled-up") of the medical devices with their positioning at a specified site in the human body or with respect to a site in the human body is possible. Another mechanism for removing ambiguities as to the location of medical devices is the size and/or shape of the particular device. For example, stents of different sizes, shape and/or construction will be utilised in different blood vessels. Such information infers or aids recognition of sites in the subject and is information which can be used to further augment image data (as above) or the logged record (as above).

In examples, the databank 8 may interface directly with third party systems 9 to display, record or document the data without requiring interaction with the local system 1,6. In examples, the specification information derived from the barcode/marker 100 is integrated with the patient's case details and entered directly onto the x-ray images or recorded into the patient's medical notes—in this manner the data derived about the detected medical devices 100 is linked to the images themselves so that the operator, third party and/or physician is provided with medical device specification information derived from the medical device 100 and the image data, linking the two.

Additional recognition and identification (non-imaging recognition): If the medical device 2 has a marker 100, then the medical device can be both detected and recognized from information 101 carried in the marker 100. The marker may not be readable by the imaging system 3 alone and could be implemented, for example, as an RFID tag applied to or part of the medical device. Systems embodying the present invention can have a machine reader in addition to the imaging system so that the human body and the medical device are imaged by the imaging system and the medical device is at least detected and possibly also identified by the machine reader (which is not necessarily the imaging system). Other forms of radio frequency communication enabling machine reading of the marker are possible such as wireless communication, near-field communication and contactless communication.

Embodiments of the invention allow the medical devices used in a patient to be detected and identified readily. Embodiments of the invention can interrogate an image to identify an implanted medical device retrospectively without any invasive procedures.

System enhancements: some scenarios and improvements which can be applied in whole or in part to embodiments of the present invention.

The Automated response/Artificial Intelligence:

The imaging system of the claimed invention recognises a code by detecting and evaluating image data of the medical device and more particularly image data of a marker 100 on the medical device 2. A code carried by the marker or a code unlocked by a key carried on the marker is checked against a central database which is operable to return information to a user, another database or an authorised third party.

Having the ability to query a database for product identification about the identified medical device 2 allows the computer 6 to check for additional information. This could include, if the device is stolen, out of date, or if a product recall exists on a device. This information can then be relayed immediately back to the hospital systems, and potentially to the medical device manufacturer that there is a potential device issue.

Once the medical device has been identified in the database, it is possible to run a series of automated checks to determine whether the device is appropriate for the situation it is being used in. This again could be an out of date device, but with image recognition which can give us details about a vessel size/location it could prompt the user that a device is now too small, or now too large, or simply that the device/consumable is being used in the wrong part of the body. This could reduce patient risk, and improve quality of health care. Moving forward and thinking about a time when surgical procedures are more automated, having the computer check the ID of the device/consumable will be an essential part of a procedure verification process to ensure the correct device has been loaded, and that it is appropriate for the procedure.

Additionally, a computer monitoring a case procedure could warn the operator about potential future problems. For example, once the device/consumable is known it could automatically recognise other devices already deployed in the body for compatibility with new devices. An example of this may be a pacemaker lead which would be incompatible with a particular pacemaker. Another example would be if an operator was trying to get 2 balloons down a catheter in which the diameter would be too small. Another example could be if a prosthetic hip replacement was used, and the computer determined immediately that the size was inappropriate for the size of the joint from additional imaging. So an automated, intelligent imaging system enhanced with image data according to the present invention could warn the operator of potential future incompatibility and, going further, propose solutions to rectify the problem or suspend the procedure until human clinical intervention is possible. The solution could be changing to a different pacemaker lead in the first example, or changing to a different catheter in the second, or a different size prosthesis in the third. In this way the computer can foresee potential problems ahead of when they occur. It would also allow operators to simulate cases beforehand, by doing a virtual run-through.

In general these intelligent systems could not only cross reference compatibility from a central database, but also learn the specific preferences of individual clinicians, by recording and reviewing what they prefer to use, and reference what has been successful in the past. They could also suggest potential new alternatives to try.

By evaluating the equipment being used the computer can also assess the risk of the cases, and pre-empt potential emergency systems, and activate emergency protocols should adverse events occur.

Whilst the medical device has its identity established from the image data, the ID code can also be entered manually from the device itself or from device packaging which expresses the barcode on the medical device in printed alphanumerics on the packaging, for example. Alternatively, the barcode on the device is replicated on the packaging and can be read by machine readable means, not necessarily the same machine readable mechanism as the imaging system. Machine reading can be scanned either by a light source or x-ray to check for compatibility, for example.

Once recognised, the system can also recognise the status of a medical device. For example, if a stent is used, the system can detect the ID of the stent from the marker. Once detected the system continues to watch the position of the stent. When the system images and identifies that the stent balloon has inflated, observing a marker on the balloon or balloon shaft, then the system status can be updated to "balloon deployed". In addition to check for balloon inflation the computer could look to identify the stent within the vessel on the x-ray. In this way it could confirm, and automatically document the stent deployment. Using co-registration, the system can identify in which artery the stent has been deployed. Additionally, the system can advise on the need for further expansion based on the size of the stent (known from the ID), size of the vessel (known from the imaging QCA), and the size of the balloon expansion (known from the live imaging). Detecting and identifying medical devices within a human body can also be useful in the security environment so as to verify the nature of foreign bodies detected within the human body. If the specification information held in the databank 8 includes a patient identifier, then combining this with an identified medical device offers security the ability to verify (or provide an additional cross-check) of the personal identity of a person being scanned at a security checkpoint. Linking a patient identifier to a record of a particular implanted medical device 2 provides quasi-biometric data about that individual which is useful to help determine the identity of a person. This link ties the identified medical device 2 to a particular individual. Patient information is preferably encrypted in the specification information and patient information is not shared with, for example, security/border guards who can receive a simple red, green or amber flag whether the scanned individual matches the patient identifier information held in the databank 8 or not, thus maintaining patient confidentiality.

Embodiments of the present invention preferably utilize machine-readable marking to provide the information 101 carried in, on or as the marker 100. The marker is preferably in the form of a tag which is encoded with the information 101. The encoding mechanism has been developed to offer a large number of permutations/combinations within a self-defining coding structure. The code has to follow the physical limitations of the imaging systems. Whereas most medical devices are relatively large (order of multiple cms), it is important that the code is capable of being used along small dimensions (order of 1 or 2 mms) of devices which are either used as consumable medical devices or implanted medical devices.

In addition to the code being developed to aid identification by the imaging system, coding patterns follow specific algorithmic boundary conditions to provide a high level or likelihood of detection, in that the code is robust and can be read unambiguously, even in the most challenging imaging conditions. The coding patterns use image ensembling, and the detection algorithms have built in check-sum capacity for local error correction prior to querying on the central database.

Preferably, the coding uses up to 4 shades of greyscale on a radiopaque marker 100 or tag. The greyscales are pre-defined in a primer code and then have a number of bits in which the information is encoded, "length encoded". Referring now to FIG. 9, a marker 100 carries information 101 in the form of a code created from blocks 105 of varying shades (greyscales). The code comprises a 6-bit start primer 106, a 20-bit encoding section 107, and a 6-bit stop primer 108.

The tables below show the number of combinations for a given number of greyscales, primer lengths, and encoded length.

TABLE 1

Net combinations from three greyscales with different length encoded sections after removal of primer-like combinations in the encoded section.

| No. of greyscales | Primer length | Length encoded | Net combinations |
|---|---|---|---|
| 3 | 6 | 11 | 172773 |
| 3 | 6 | 12 | 526338 |
| 3 | 6 | 13 | 1588491 |
| 3 | 6 | 14 | 4776408 |
| 3 | 6 | 15 | 14341617 |
| 3 | 6 | 16 | 43038702 |
| 3 | 6 | 17 | 129131415 |
| 3 | 6 | 18 | 387411012 |
| 3 | 6 | 19 | 1162251261 |
| 3 | 6 | 20 | 3486773466 |

TABLE 2

Net combinations from four greyscales with different length encoded sections after removal of primer-like combinations in the encoded section.

| No. of greyscales | Primer length | Length encoded | Net combinations |
|---|---|---|---|
| 4 | 6 | 11 | 4,169,728) |
| 4 | 6 | 12 | 16,748,544) |
| 4 | 6 | 13 | 67,076,096) |
| 4 | 6 | 14 | 268,398,592) |
| 4 | 6 | 15 | 1,073,700,864) |
| 4 | 6 | 16 | 4,294,922,240) |
| 4 | 6 | 17 | 17,179,820,032) |
| 4 | 6 | 18 | 68,719,423,488) |

TABLE 2-continued

Net combinations from four greyscales with different length encoded sections after removal of primer-like combinations in the encoded section.

| No. of greyscales | Primer length | Length encoded | Net combinations |
|---|---|---|---|
| 4 | 6 | 19 | 274,877,849,600) |
| 4 | 6 | 20 | 1,099,511,566,336) |

The code on the tag is preferably an elongate strip of bits/blocks 105 with each block having a 1 mm width along the length of the strip and a minimum height of 1 mm across the strip. The block may not be a block of material but a space the size of a block meaning that the space the size of a block has 100% relative opacity. Opacity will be discussed later. The strip height is constrained by the size of the device/disposable upon which the code is being marked. For example in a pacemaker, the height could be large because the dimensions are in the order of cms, whereas, in a coronary catheter the height would be smaller because the dimensions are in the order of mms.

The choice of dimensions of the marker depends on the size of the device/disposable 2. The example marker 100 of FIG. 9 with a code comprising a 6-bit start primer 106, a 20-bit encoding section 107, and a 6-bit stop primer 108 results in a 32 mm elongate tag which fits on the vast majority of medical devices 2 and medical consumables. However, as can be seen from the tables above, there is considerable scope for choosing a tag with smaller dimensions (electing less combinations) as determined by the dimensional constraints of the medical device 2 to which the tag 100 is applied.

The primer may be short, two or three bits. The example of FIG. 9 uses six bits or blocks 105 to comprise the primer 106. The unique nature of the coding system on x-ray provides a far higher number of combination that would be present from a single array of black and white bars. The computer identifies the nature of the code it expects from the primer sequence. The primer sequence is an array of codes which tell the computer what to expect from the following encoded section of the marker array. A primer sequence is at the start and end of the encoded section and can run in the same direction, or in mirror image direction, it can be the same as or different at either end. These patterns aid the computer to know how to interpret the encoded section.

The primer registration tells the computer what to expect in terms of length from the encoded section and also tells the computer the number of greyscale channels to expect, and also how to interpret the different imaged densities.

As x-rays pass through tissue differently in every person, a particular shade of grey on one person will differ from a shade of grey on another person. This means that that if we were using absolute colours it would be impossible to know what greyscale colour was being encoded. The primer overcomes this by defining the greyscale shades/intensities/densities such that the computer knows where each shade sits in terms of intensity/density or level. For example, in the first position of the primer there is a solid black block 105, in the second a white block and in the third a block with a shade of grey. These are each produced by altering the density of the material of each band, and in doing so letting more/less of the x-ray pass through. The same densities are used on the primer section as are used on the encoded section, such that when the computer recognises black in the primer region it knows the intensity of black in the encoded section. Similarly, for white blocks and any of the greyscale intensities. The computer can thus on each individual frame have the key (the primer) to unlocking the code (encoded section). This approach drastically increases the density of combinations which can run to over a trillion unique combinations from a relatively simple sequence.

Marker placement and orientation is also an important consideration. When a device 2 is imaged, there can be no guarantee that a marker 100 on the device 2 will be correctly oriented with respect to the imaging device so as to allow the complete code to be imaged, processed and determined unambiguously.

The precise manner in which the marker strips 100 are mounted on medical devices varies depending on the nature of the medical device 2 to which they are being attached (or embedded). Some mounting scenarios:
  i. flat or lightly contoured plastic plate
  ii. elongate cylinder, e.g. a coronary catheter
  iii. flat or lightly contoured metallic plate, e.g. on a pacemaker Accordingly, multiple markers 100 should preferably be provided on a single device 2 with different orientations and placements so that the chances of at least one marker "facing" an imaging system for unambiguous identification are increased. The differently placed markers may each have a unique code 101 indicating where each marker 100 is located on the device 2 (e.g. proximal end, distal end, mid-point of device). This provides good location resolution of the different parts of the device which can be important for a long device such as a catheter. Alternatively, the differently placed markers may each have the same code, for example on adjacent flat sides of a pacemaker (but not overlapping).

Marker placement on a medical device is effected to avoid or minimize x-ray shadowing which can be caused if a part of a marker overlaps another marker in the imaged field. Shadowing can lead to ambiguities in the code being read. Labelling or marking of medical devices 2 can be done on the outside of the device 2, or preferably within the device 2. If a device has already had approval from a medical authority for use within the human body, then printing a marker onto an internal surface of a device may not need further approval from the regulatory authority. Printing a marker on an external surface may require further approval from the regulatory authority. The code is preferably machine read by, for example, an x-ray imaging system, and so the code can be read equally well within the device as on an external surface of the device 2.

Where possible an array of markers is positioned at multiple positions in an orthogonal array, such that x-ray beams incident at differing angles should always be able to acquire an on-axis view. In the case of a catheter there would be an array of markers positioned close to the tip, and a series along the shaft of the catheter. In the case of a pacemaker this could be a marker array fixed on the inside of the pacemaker on two orthogonal surfaces (side wall and adjacent main flat surface for example).

For elongate medical devices such as catheters, sutures, and bronchial tubes, circumferential placement of markers should be avoided. Markers should be placed along the length of the device, normal to the circumference, to minimize the risk of shadowing—see FIG. 10 in which two elongate tags are mounted as markers along the length of the cylindrical device. The two tags 100 are preferably radially offset from one another by 45° and are axially spaced apart thereby minimizing the risk of shadowing and maximizing the chances of squarely facing the imaging system.

Figure 10:
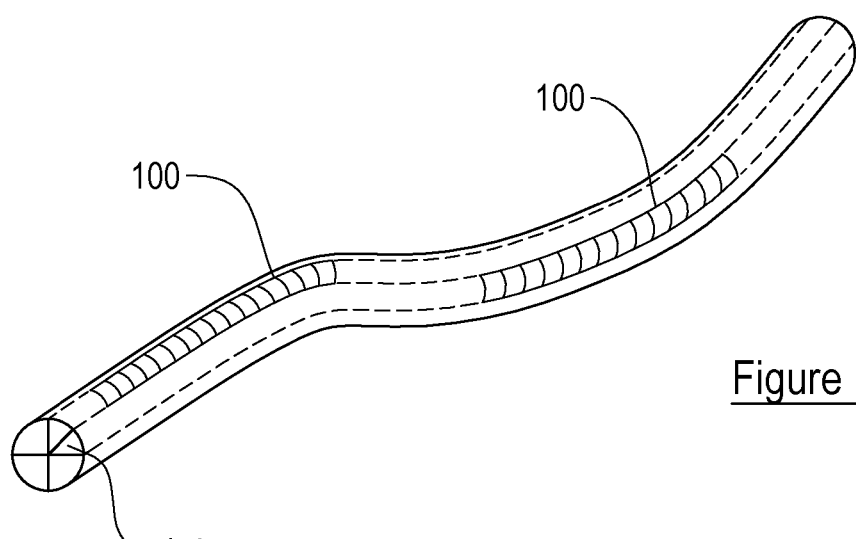
FIG. 10 is a schematic example embodying the present invention of an elongate cylindrical medical device carrying two markers.
Figure 11:
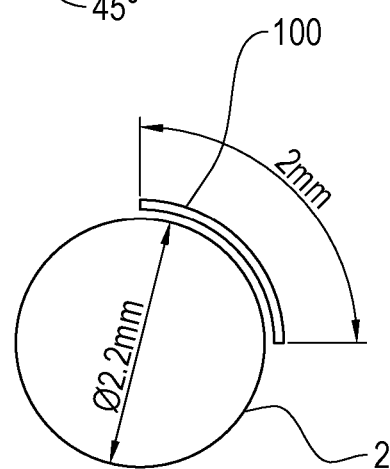
FIG. 11 is a schematic cross section through an example elongate cylindrical medical device carrying a marker.
Figure 12:
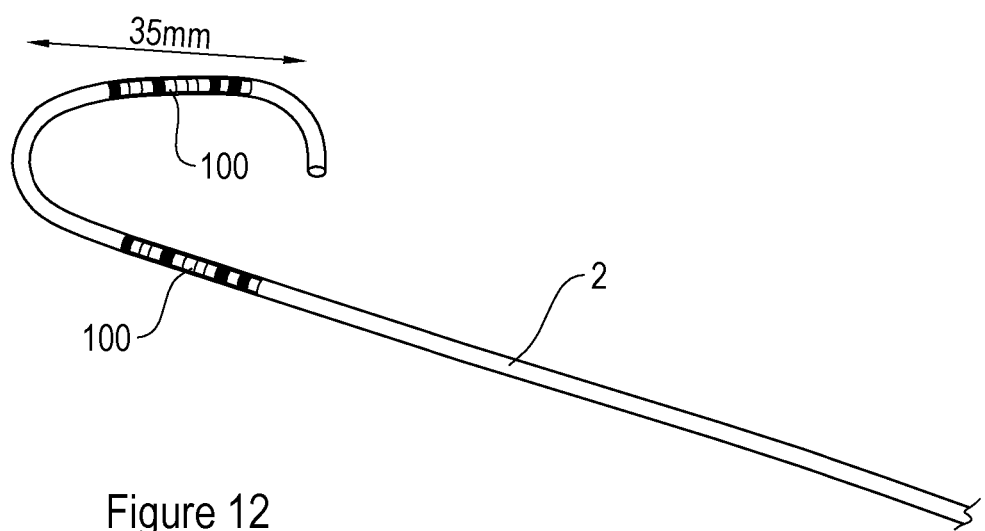
FIG. 12 is another schematic example embodying the present invention of an elongate cylindrical medical device carrying two markers.

In combination with marker placement, the dimensions of the marker 100 are deliberately curtailed so that they do not extend over more than a quarter of the circumference of the substantially cylindrical medical device 2. If the marker 100 extended around the circumference, then there is a much greater risk of shadowing. Referring to FIG. 11, an elongate strip marker 100 (as shown in FIGS. 9 and 10) is mounted on a 6F guide catheter 2 which has a diameter of 2.2 mm, hence a circumference of 6.9 mm. The marker strip height is limited to 2 mm ($<(\frac{1}{4})*2\pi r$) so that the risk of shadowing is minimized. FIG. 12 shows two markers 100 mounted at two discrete positions along the length of a catheter 2. One mounting consideration is the natural flex and shape of the catheter such as shown in FIG. 12. One marker is positioned towards the distal end of the catheter before the first bend and the other is positioned further around after the first bend of the catheter.

In preferred embodiments the code is configured as a bar code (the series of blocks 105) which can be directly printed onto the medical device 2. The bar code is composed of the blocks/bits described above (105,106,107,108) and may be painted, sprayed or printed onto the medical device as a thin film. A number of techniques can be used to deposit a thin film, foil or coating, preferably metallic in nature, onto the medical device. The absence of a film, one layer of film or multiple layers of film determine the relative opacity of the resultant block 105.

The term "printed" will now be used to describe the mechanism for laying down a thin film of material (to make up a block 105 of the marker 100) onto a substrate of the medical device 2.

Preferably, each block of the code is made up from none, one or multiple layers of material printed onto the medical device. Each layer of material has a predetermined thickness and is tailored to contribute to a predetermined percentage of relative opacity (a measure of how opaque to the particular imaging system each layer of printed material is) when imaged by a designated imaging system. Different opacities provide different greyscales. Labelling with a marker 100 takes the form of a series of bars or blocks 105 detectable by the imaging system. These blocks are made up of varying densities, such that differing amounts of x-ray can pass through each block. The x-ray image shows and the system can decipher a series of differing greyscale shades from each block. At the extreme would be white (low density, 100% opacity), to black (high density, 0% opacity), and then in the middle different shades of grey depending on the density of the block.

Figure 13:
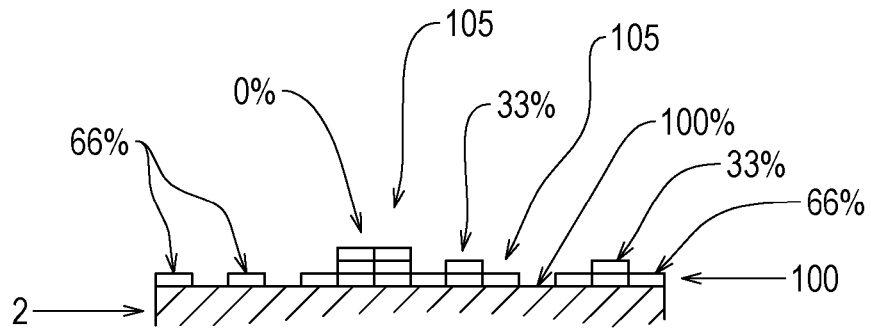
FIG. 13 is a schematic cross section through a part of a medical device and a marker employing four greyscales, showing the varying levels of opacity with varying film thicknesses.

For example, when using an x-ray imaging system with a code having four greyscales, see FIG. 13, a film thickness is selected which provides 33% relative opacity. The base is 100% opacity where there is no film deposited so there is just the opacity of the medical device 2 itself on which the marker 100 is printed. One film thickness removes 33% opacity. Two film thicknesses remove 66% opacity. The third film thickness removes the last 33% opacity leading to 0% opacity for three film thicknesses. In this way, multiple blocks can be printed with four different opacity levels (0%, 33%, 66% & 100%), i.e. four greyscales—see FIG. 9 also.

Figure 14:
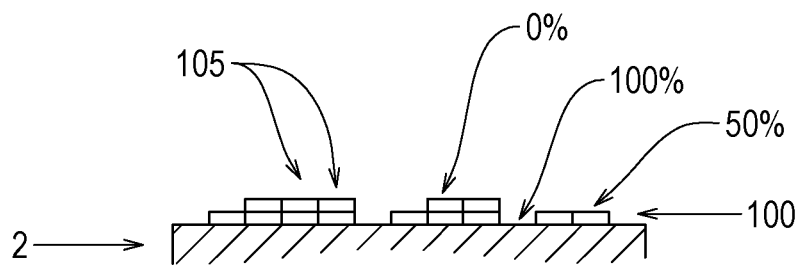
FIG. 14 is a schematic cross section through a part of a medical device and a marker employing three greyscales, showing the varying levels of opacity with varying film thicknesses.
Figure 15:
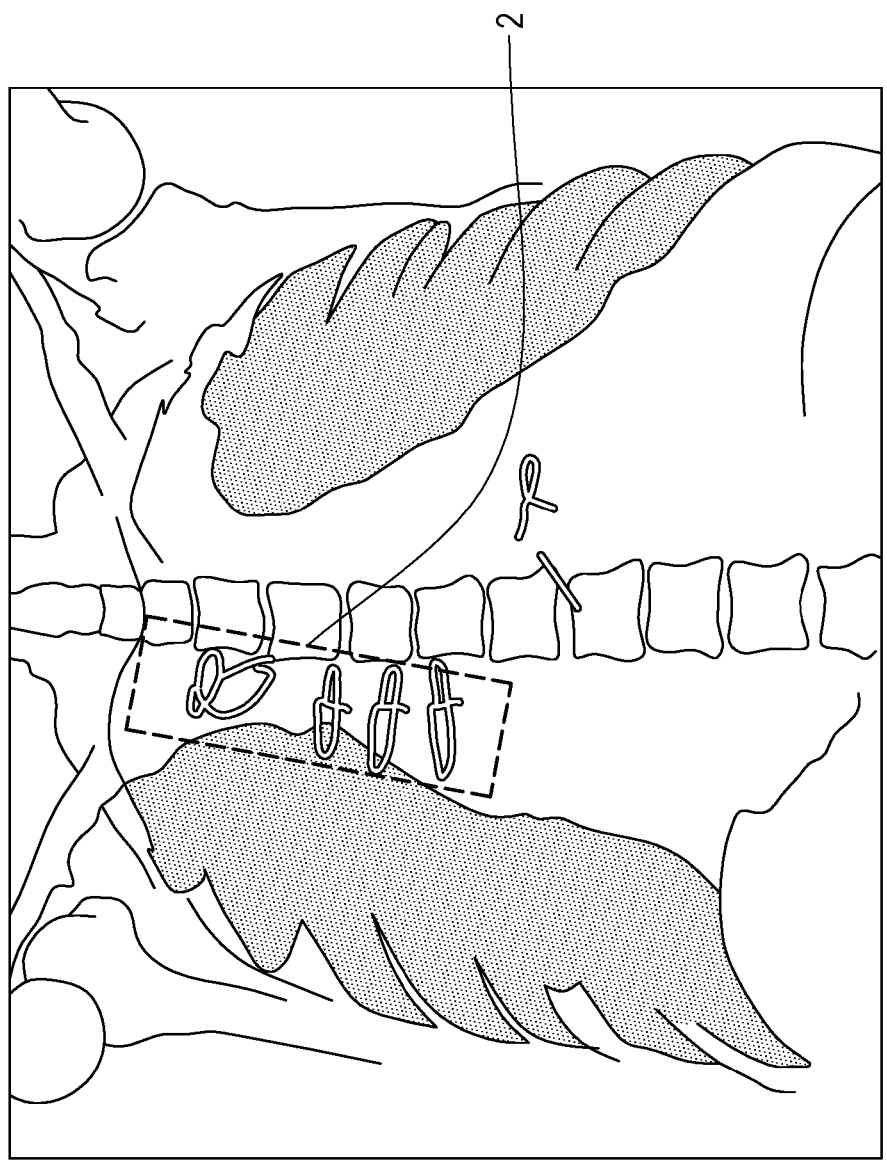
FIGS. 15-26 illustrate and describe embodiments of the invention.
Figure 16:
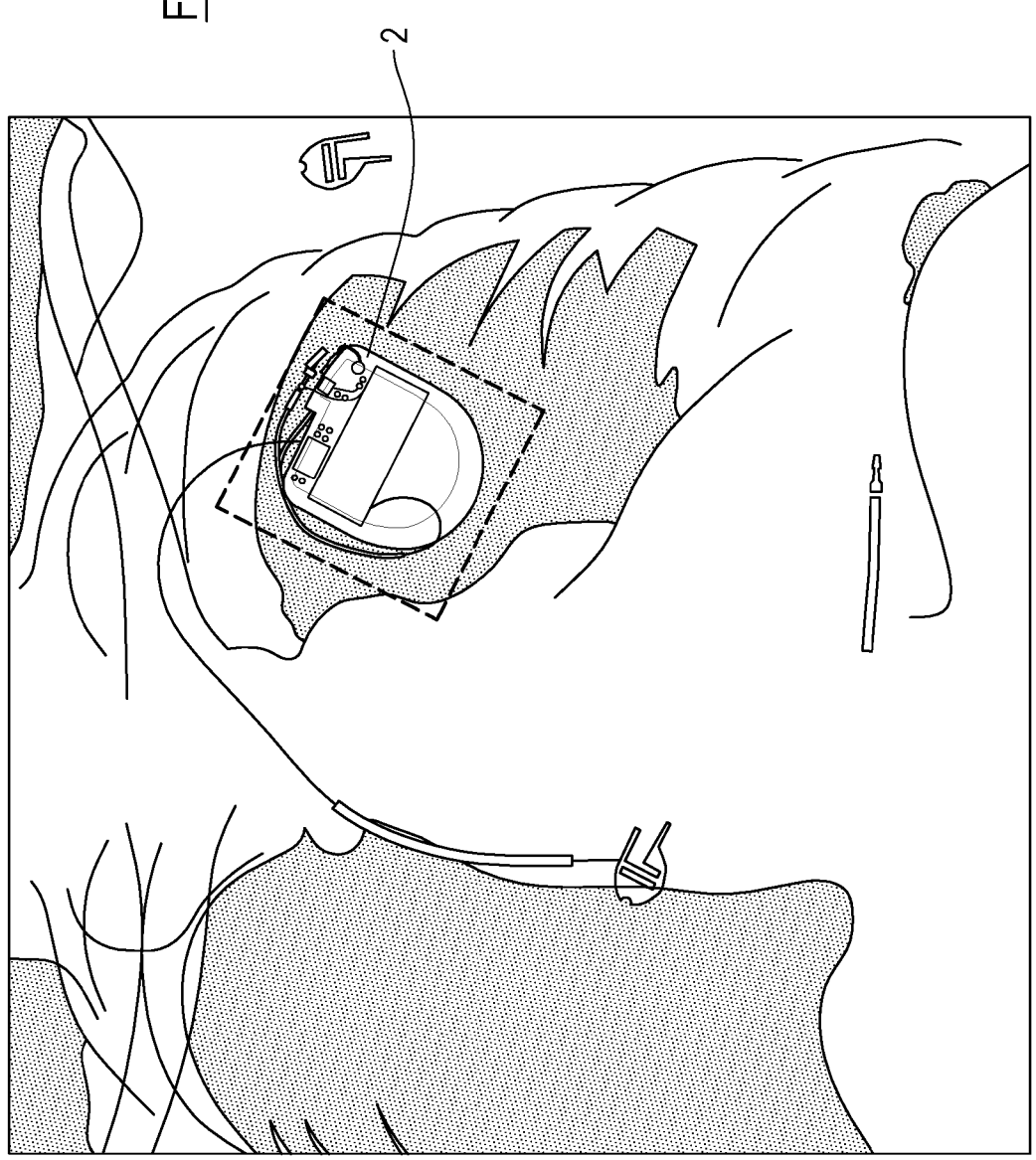
Figure 17:
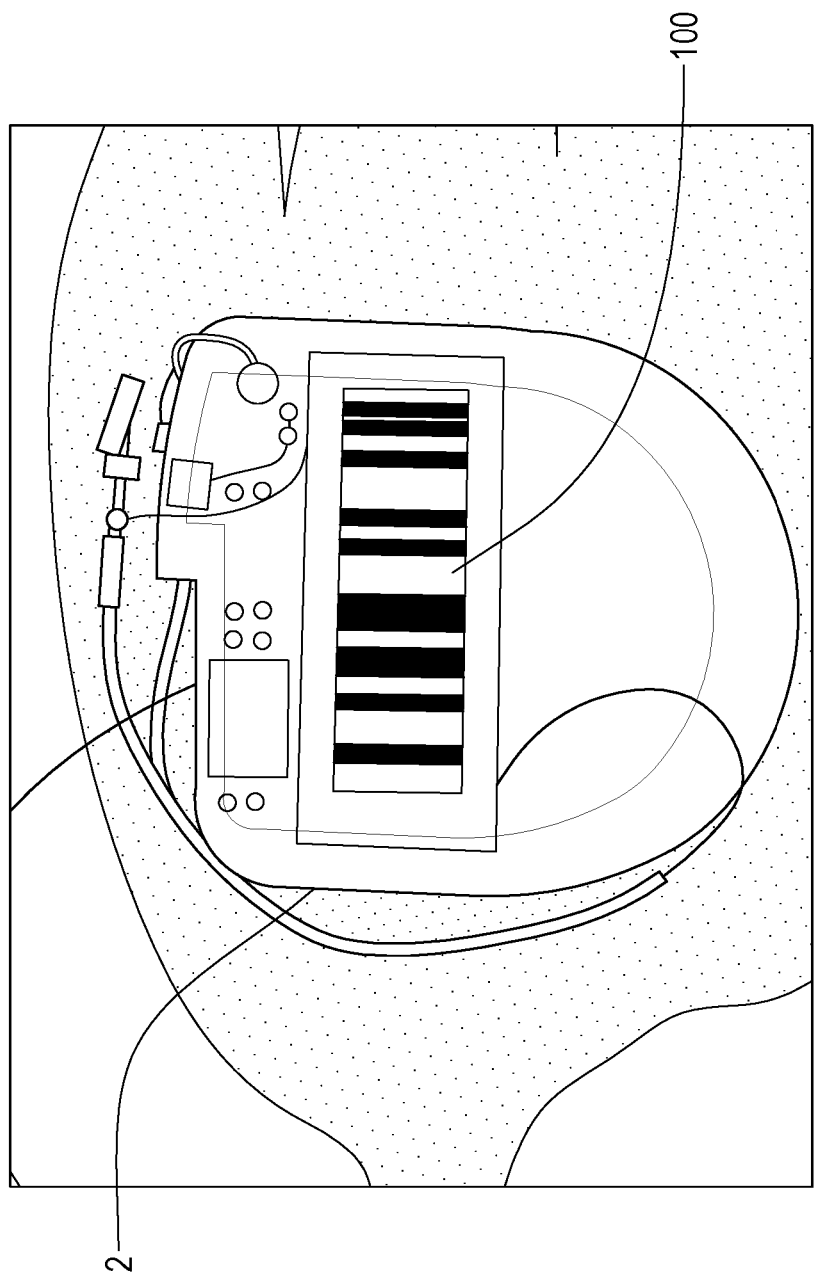
Figure 18:
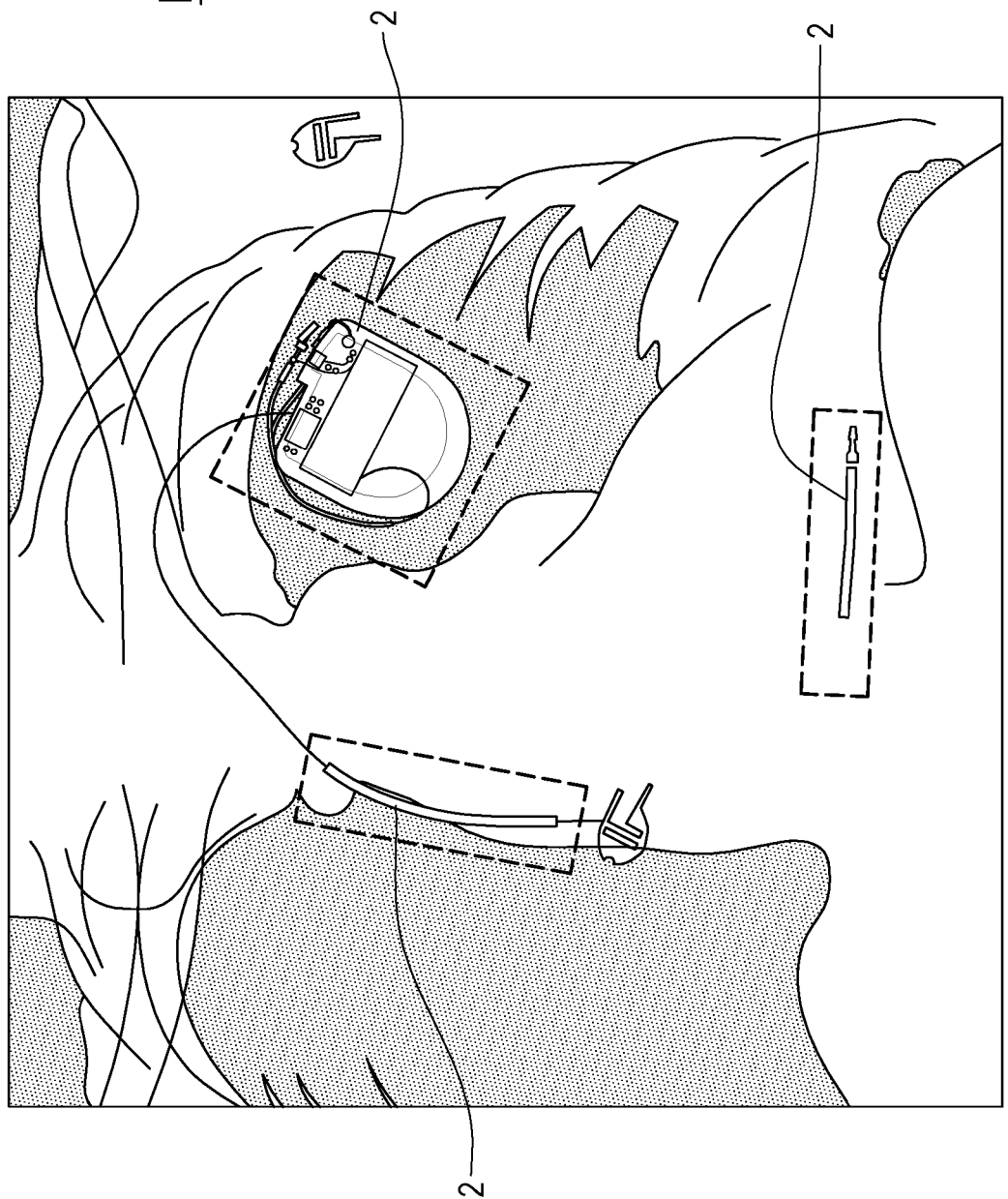
Figure 19:
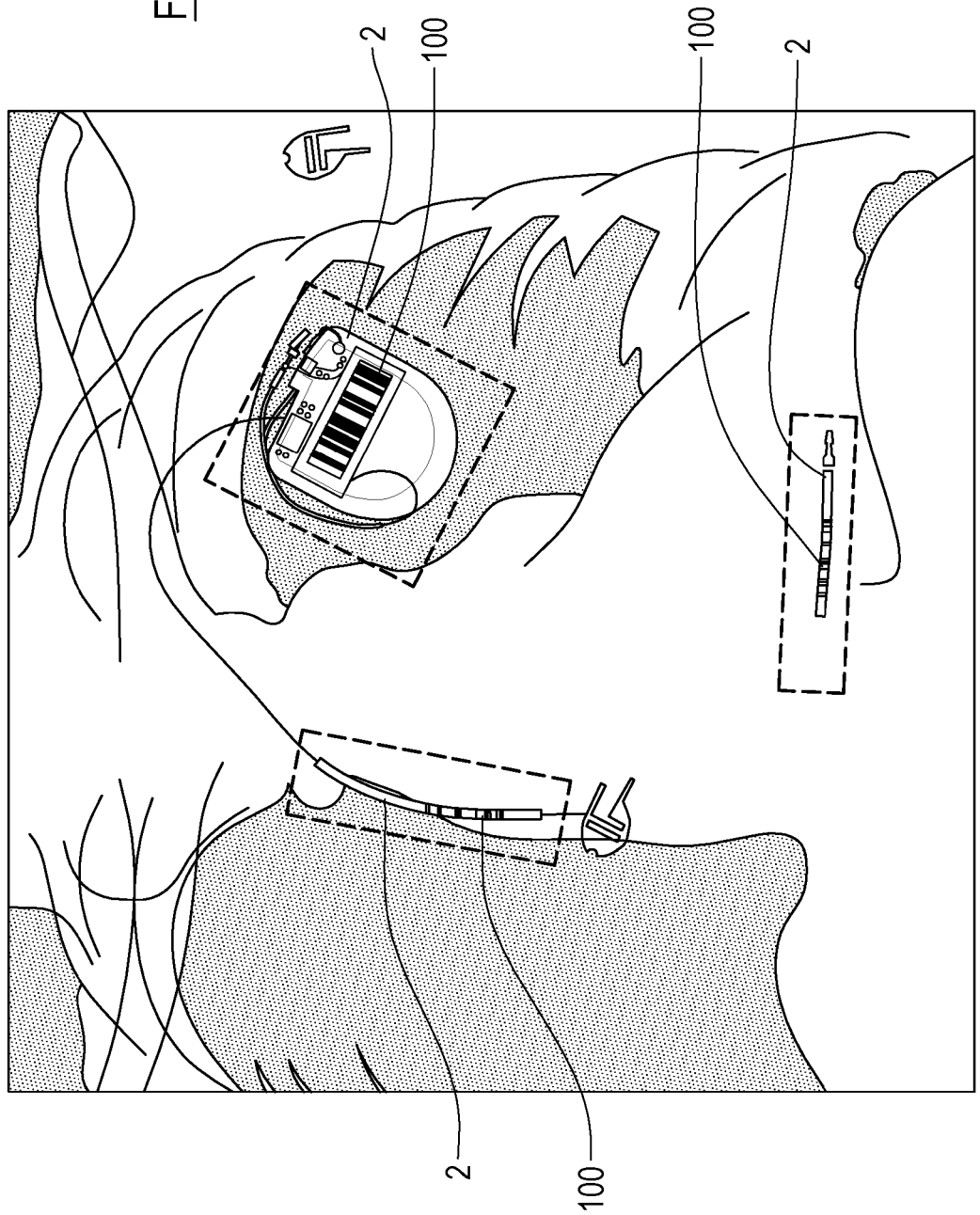
Figure 20:
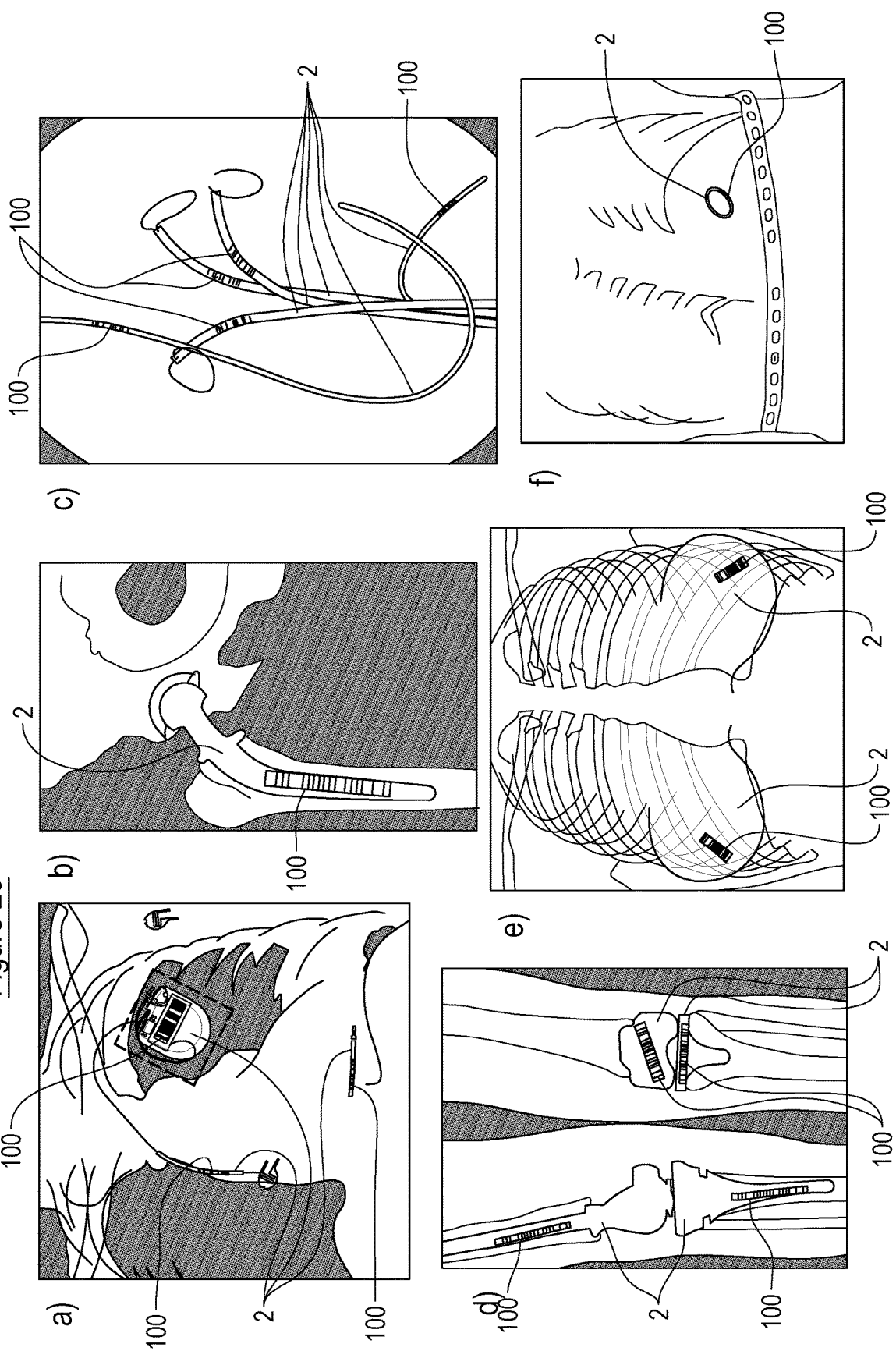
Figure 21:
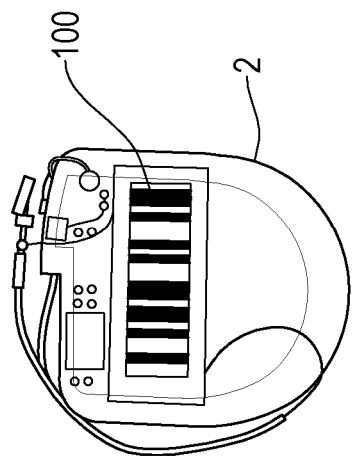
Figure 22:
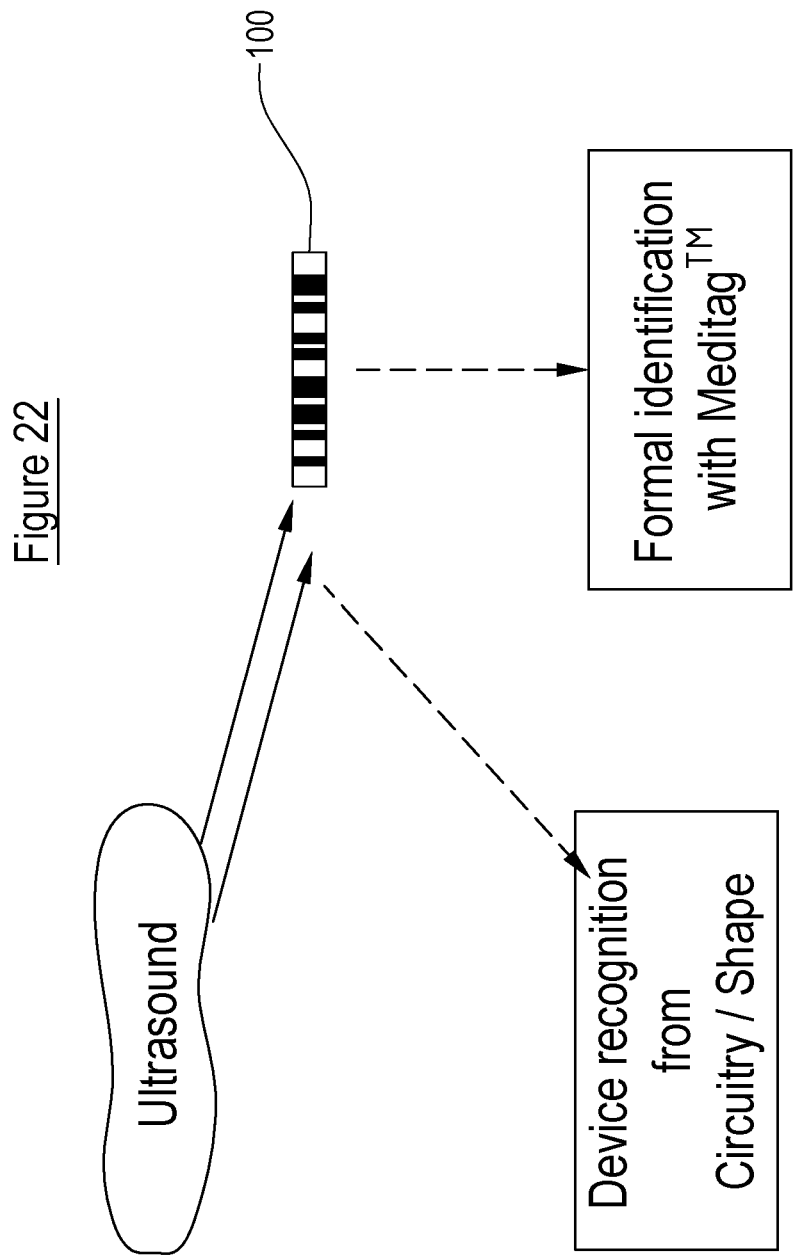
Figure 23:
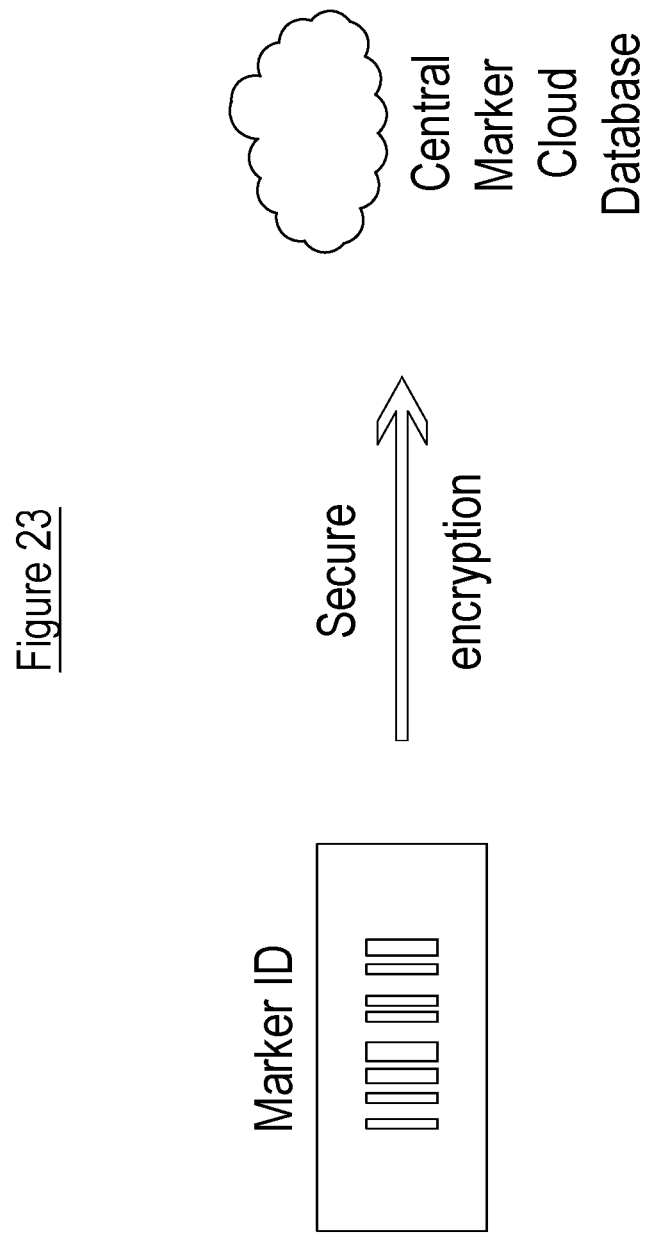
Figure 24:
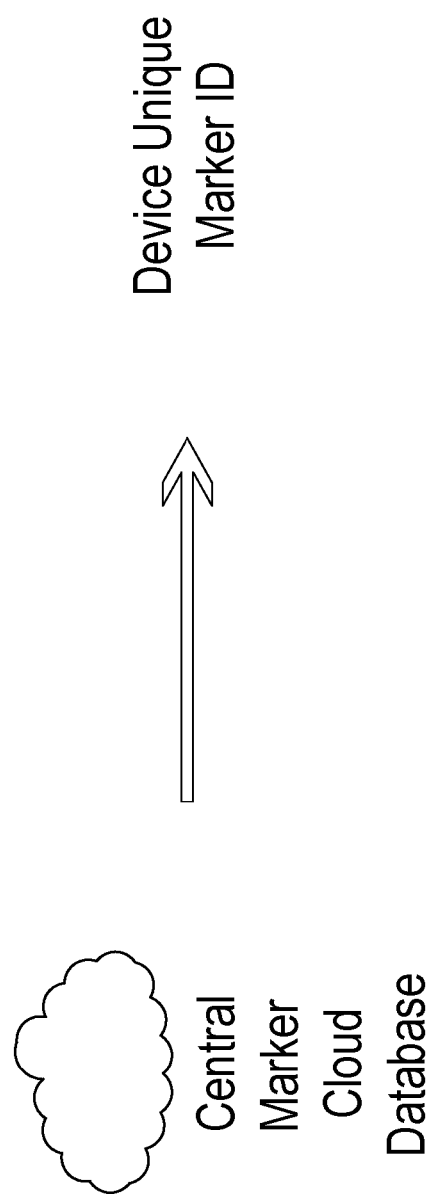
Figure 25:
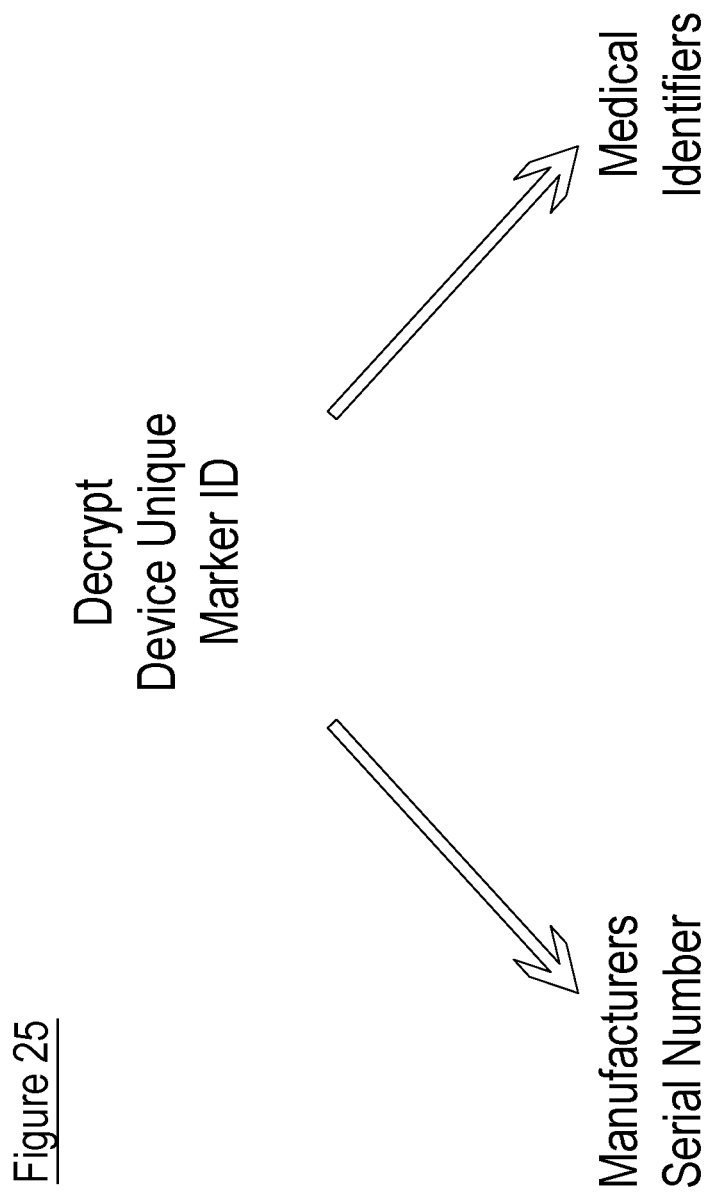
Figure 26:
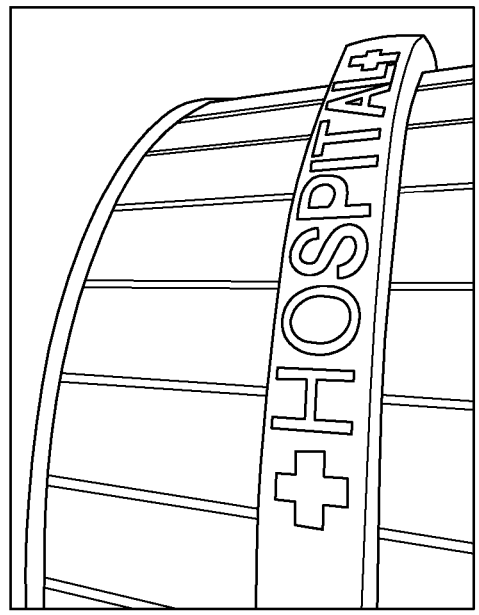
Figure 26:
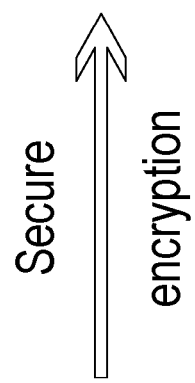
Figure 26:
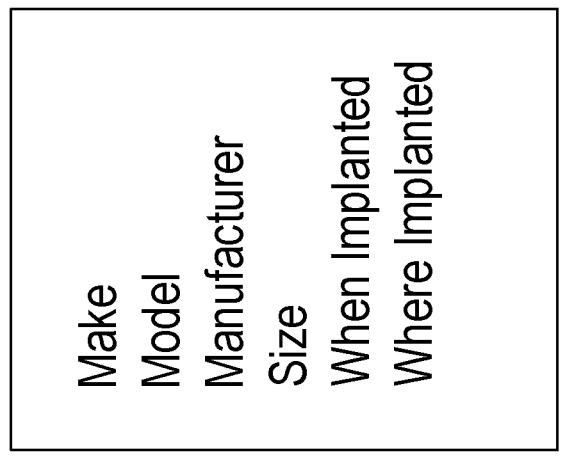

In another example, when using an x-ray imaging system with a code having three greyscales, see FIG. 14, a film thickness is selected which provides 50% opacity. The base is 100% opacity where there is no film deposited so it is just the opacity of the medical device 2 on which the marker 100 is printed. One film thickness removes 50% opacity. Two film thicknesses remove 100% opacity leading to 0% opacity for two film thicknesses. In this way, multiple blocks can be printed with three different opacity levels (0%, 33%, 66% 100%), i.e. three greyscales.

As well as printing onto a substrate of the medical device 2, there are techniques for printing onto a metal, for example, embedded in the medical device substrate—a strip of foil, for example. Ultrasonic additive manufacturing is a 3D printing technology that uses ultrasound to modulate layers of metal within the foil strip. The modulation changes the imaged density of portions of the strip with respect to other portions of the strip so that they present different images or density of shading when imaged. The process works with a variety of metals such as aluminium, copper and titanium. Similarly, the material of the medical device 2 itself can be modulated by etching (selective removal of material) to alter/modulate its imaged properties. Altering the imaged properties of blocks of material within or on a substrate allows a code or information to be encoded in or on the medical device material to form a marker 100.

In some cases it may be desirable for the marker 100 to carry a smaller encoded section or primer section, perhaps due to space limitations on a medical device 2 on which the marker 100 is located. In such cases, the code (primer or encoded section) 101 can act as a key to access or unlock another, possibly more complex, code embedded in an RFID tag associated with the same medical device 2, i.e. the same medical device carries an imaging marker and an RFID marker. The code from the RFID tag can be used to interrogate the central database in place of the code from the imaging marker. Thus the code on the imaging marker does not interrogate the database for the medical device directly but the imaging marker code works alongside the RFID code. In this way, the imaging marker code is not acting to identify the medical consumable/device but acts as a password/key to unlock the identity of the medical device on the database. This two-stage verification process can be useful to prevent fraud and ensure data integrity.

In the present specification "comprise" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A marker attached to, embedded in or comprising a medical device to identify the medical device within a biological subject from imaging data of the marker, the marker having information encoded in the opacity of the marker detectable to an imaging system,
    wherein the marker comprises a linear array of bits along an x-axis, with layers of radiopaque material stacked in a z-axis, the z-axis substantially perpendicular to the surface of the layers of radiopaque material, the stacked layers of radiopaque material making bits of different value; and a primer predefining up to four shades of greyscale used in the marker.

2. The marker of claim 1, wherein the marker or information derived from the marker is machine-readable.

3. The marker of claim 1, wherein the marker is machine-readable by the imaging system and/or by radio frequency communication comprising wireless communication, near-field communication and/or contactless communication.

4. The marker of claim 1, wherein the radiopaque material of the marker has a marker surface texture and a marker surface contour, wherein the opacity of the radiopaque material of the marker, the opacity of the marker surface texture, or the opacity of the marker surface contour is modulated to encode information.

5. The marker of claim 1, wherein the marker is: a code, or a watermark image.

6. The marker of claim 1, wherein the marker comprises a unique identifier for the medical device and/or comprises an indicator of a class of the medical device.

7. The marker of claim 1, wherein the marker comprises orientation information for the medical device.

8. The marker of claim 1, wherein the primer is at the start of the linear array of bits.

9. The marker of claim 8, wherein the marker further comprises a second primer at the end of the linear array of bits.

10. The marker of claim 1, wherein the linear array of bits is 11 to 20 bits long.

11. A plurality of markers according to claim 1, each attached to, embedded in or comprising the medical device, wherein the markers have different orientations on the device.

12. A system for detecting a medical device to detect the medical device within a biological subject and to identify the medical device from imaging data, the system comprising:
a marker attached to, embedded in or comprising the medical device having information encoded in the opacity of the marker detectable by imaging, and the marker comprising a linear array of bits along an x-axis, with layers of radiopaque material stacked in a z-axis, the z-axis substantially perpendicular to the surface of the layers of radiopaque material, the stacked layers of radiopaque material making bits of different value; and a primer predefining up to four shades of greyscale used in the marker;
an imaging system configured to generate image data of the marker derived from image data of the medical device within the biological subject; and
a processor configured to evaluate the image data of the marker to detect and identify the medical device.

13. The system of claim 12, wherein the system is configured to generate a signature from the image data of the marker and/or from information encoded in the marker, the signature being related to the detected medical device.

14. The system of claim 13, wherein the signature is an indicator of a class of the detected medical device.

15. The system of claim 13, wherein the signature is an indicator of a unique identifier of the detected medical device.

16. The system of claim 13, further comprising a databank holding signature information for a plurality of medical devices and corresponding specification information and/or characteristics for the plurality of medical devices, the system being configured to match a signature relating to a detected medical device with signature information held in the databank and to provide some or all of the specification information and/or characteristics for the matched signature.

17. The system of claim 16, wherein the system is configured to augment the image data with some or all of the specification information for the matched signature, the augmented information being in respect of and/or associated with the detected medical device.

18. A method of identifying a medical device within a biological subject, the medical device having a marker attached to, embedded in or comprising the medical device, the marker having information encoded in the opacity of the marker detectable by an imaging system, and the marker comprising a linear array of bits along an x-axis, with layers of radiopaque material stacked in a z-axis, the z-axis substantially perpendicular to the surface of the layers of radiopaque material, the stacked layers of radiopaque material making bits of different value; and a primer predefining up to four shades of greyscale used in the marker, the method comprising:
imaging the biological subject to generate image data of the marker attached to, embedded in or comprising the medical device in the biological subject;
processing the image data to detect the marker; and
using a processor, identifying the medical device from the marker.

19. The method of claim 18, further comprising:
matching a signature relating to the detected marker with signature information held in a databank for a plurality of medical devices, the databank also holding specification information corresponding to the plurality of medical devices; and
providing some or all of the specification information for the matched signature to identify the medical device.

20. The method of claim 18, further comprising:
deriving a signature from the marker;
interrogating a databank holding specification information corresponding to a plurality of medical devices;
matching the signature from the marker with signature information held in the databank; and
providing some or all of the specification information for the matched signature to augment the image data.

* * * * *